(12) United States Patent
Dunlop et al.

(10) Patent No.: US 9,428,726 B2
(45) Date of Patent: Aug. 30, 2016

(54) MODIFIED HOST CELLS WITH EFFLUX PUMPS

(75) Inventors: Mary J. Dunlop, Burlington, VT (US); Jay D. Keasling, Berkeley, CA (US); Aindrila Mukhopadhyay, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/115,925

(22) Filed: May 25, 2011

(65) Prior Publication Data

US 2011/0294183 A1    Dec. 1, 2011

Related U.S. Application Data

(60) Provisional application No. 61/248,201, filed on May 25, 2010.

(51) Int. Cl.
| | | |
|---|---|---|
| C12N 1/20 | (2006.01) | |
| C12P 5/00 | (2006.01) | |
| C12P 7/04 | (2006.01) | |
| C12P 7/62 | (2006.01) | |

(52) U.S. Cl.
CPC ............... *C12N 1/20* (2013.01); *C12P 5/007* (2013.01); *C12P 7/04* (2013.01); *C12P 7/62* (2013.01)

(58) Field of Classification Search
None
See application file for complete search history.

(56) References Cited

U.S. PATENT DOCUMENTS

| | | | |
|---|---|---|---|
| 4,551,433 A | 11/1985 | DeBoer | |
| 2007/0099277 A1* | 5/2007 | Anderson et al. | 435/108 |

OTHER PUBLICATIONS

NP_743544 (created on Feb. 14, 2002).*
Tudroszen et al., α-Pinene metabolism by Pseudomonas putida., Biochem. J. (1977), vol. 168, pp. 315-318.*
Teran et al., Antibiotic-Dependent Induction of Pseudomonas putida DOT-T1E TtgABC Efflux Pump is Mediated by the Drug Binding Repressor TtgR, Antimicrob Agents Chemother. (Oct. 2003), vol. 47(10), pp. 3067-3072.*
TtgB of Teran et al. (last viewed on Jan. 19, 2013).*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Ramos et al., Mechanisms of Solvent Tolerance in Gram-Negative Bacteria., Annu. Rev. Microbiol. (2002), vol. 56, pp. 743-768.*
Rojas et al., Biotransformation in Double-Phase Systems: Physiological Responses of Pseudomonas putida DOT-T1E to a Double Phase Made of Aliphatic Alcohols and Biosynthesis of Substituted Catechols., Appl Environ Microbiol. (2004), vol. 70(6), pp. 3637-3643.*

(Continued)

*Primary Examiner* — Alexander Kim
(74) *Attorney, Agent, or Firm* — Robin C. Chiang; Lawrence Berkeley National Laboratory

(57) ABSTRACT

The present invention provides for a modified host cell comprising a heterologous expression of an efflux pump capable of transporting an organic molecule out of the host cell wherein the organic molecule at a sufficiently high concentration reduces the growth rate of or is lethal to the host cell.

18 Claims, 10 Drawing Sheets

(56) References Cited

OTHER PUBLICATIONS

Peralta-Yahya, P.P. and J.D. Keasling, "Advanced biofuel production in microbes." Biotechnology Journal 5(2): p. 147-162, (2010).
Ramos, J.L., et al., "Mechanisms of solvent tolerance in gram-negative bacteria.". Annu Rev Microbial, 2002. 56: p. 743-768.
Fortman, J.L., et al., "Biofuel alternatives to ethanol: pumping the microbial well.".Trends in Biotechnology, 2008. 26(7): p. 375-381.
Lee, S.K., et al., "Metabolic engineering of microorganisms for biofuels production: from bugs to synthetic biology to fuels." Current Opinion in Biotechnology, 2008. 19(6): p. 556-563.
Stephanopoulos, G., "Challenges in engineering microbes for biofuels production." Science, 2007. 315(5813): p. 801-804.
Dunlop, M.J., J.D. Keasling, and A. Mukhopadhyay, "A model for improving microbial biofuel production using a synthetic feedback loop." Systems & Synthetic Biology, 2010.
Harvey, B.G., M.E. Wright, and R.L. Quintana, "High-Density Renewable Fuels Based on the Selective Dimerization of Pinenes." Energy & Fuels. 24: p. 267-273, (2010).
Paulsen, I.T., M.H. Brown, and R.A. Skurray, "Proton-dependent multi drug efflux systems." Microbiological Reviews, 1996. 60( 4), p. 575-608.
Bavro, V.N., et al., "Assembly and channel opening in a bacterial drug efflux machine." Molecular Cell, 2008. 30(1): p. 114-121.
Putman, M ., H.W. Van Veen, and W.N. Konings, "Molecular properties of bacterial multidrug transporters." Microbiology And Molecular Biology Reviews, 2000. 64(4): p. 672-693.
Ramos, J.L., et al., "Efflux pumps involved in toluene tolerance in Pseudomonas putida DOT-T1E." Journal Of Bacteriology, 1998. 180(13): p.3323-3329.
Rojas, A., et al., "Three efflux pumps are required to provide efficient tolerance to toluene in Pseudomonas putida DOT-T1E." Journal of Bacteriology, 2001. 183(13): p. 3967-3973.
Kieboom, J., et al., "Identification and molecular characterization of an efflux pump involved in Pseudomonas putida S12 solvent tolerance." Journal Of Biological Chemistry, 1998.273(1): p. 85-91.
Kieboom, J., et al., "Active efflux of organic solvents by Pseudomonas putida S12 is induced by solvents." Journal Of Bacteriology, 1998. 180(24): p. 6769-6772.
Ikken, S. And J.A.M. De Bont, "The solvent efflux system of Pseudomonas putida S12 is not involved in antibiotic resistance." Applied Microbiology And Biotechnology, 2000. 54(5): p. 711-714.
Li, X.Z., L. Zhang, and K. Poole, "Role of the multidrug efflux systems of Pseudomonas aeruginosa in organic solvent tolerance." Journal Of Bacteriology, 1998.180(11): p. 2987-2991.

Nikaido, H. and Y. Takatsuka, "Mechanisms of RND multidrug efflux pumps." Biochimica Et Biophysica Acta-Proteins and Proteomics, 2009. 1794(5): p. 769-781.
Tseng, T.-T., et al., "The RND Permease: Superfamily: An Ancient, Ubiquitous and Diverse Family that Includes Human Disease and Development Proteins." J. Mol. Microbial. Biotechnolo., 1999. 1(1): p. 107-125.
Hardin, G., "Competitive Exclusion Principle" Science, 1960. 131(3409): p. 1292-1297.
Levin, S.A., "Community Equilibria and Stability, And An Extension Of competitive Exclusion Principle." American Naturalist, 1970. 104(939): p. 413-423.
Rutherford, B.J., et al., "Functional Genomic Study of Exogenous n-Butanol Stress in *Escherichia coli*" Applied And Environmental Microbiology, 2010. 76(6): p. 1935-1945.
Bokma, E., et al., "Directed evolution of a bacterial efflux pump: Adaptation of the *E•coli* ToIC exit duct to the Pseudomonas MexAB translocase." Febs Letters, 2006. 580(22): p. 5339-5343.
Atsumi, S., T. Hann, and J.C. Liao, "Non-fermentative pathways for synthesis of branched-chain higher alcohols as biofuels." Nature, 2008. 451: p. 86-90.
Steen, E.J., et al., "Metabolic engineering of *Saccharomyces cerevisiae* for the production of n-butanol." Microbial Cell Factories, 2008. 7(36).
Lee, A., et al., "Interplay between efflux pumps may provide either additive or multiplicative effects on drug resistance." Journal Of Bacteriology, 2000. 182(11): p. 3142-3150.
Dehal, P.S., et al., "MicrobesOnline: an Integrated portal for comparative and functional genomics." Nucleic Acids Research, 2010. 38: p. D396-D400. (published online Nov. 11, 2009).
Krogh, A, et al., "Predicting transmembrane protein topology with a hidden Markov model: Application to complete genomes." Journal Of Molecular Biology, 2001. 305(3): p. 567-580.
Altschul, S.F., et al, "Gapped Blast and Psi-Blast: a new generation of protein database search programs." Nucleic Acids Research, 1997. 25(17): p. 3389-3402.
Datsenko, K.A. and B.L. Wanner, "One-step inactivation of chromosomal genes in *Escherichia coli* K-12 using PCR products." Proceedings Of The National Academy Of Sciences Of The United States of America, 2000. 97(12): p. 6640-6645.
Baba, T., et al. "Construction of *E scherichia coli* K-12 in-frame, single-gene knockout mutants: the Keio collection." Molecular Systems Biology, 2006.
Li, M.Z., et al. "Harnessing homologous recombination in vitro to generate recombinant DNA via SLIC." Nature Methods, 2007. 4(3): p. 251-256.

* cited by examiner

SEQUENCE LISTING

```
<160> NUMBER OF SEQ ID NOS: 7

<210> SEQ ID NO 1
<211> LENGTH: 1055
<212> TYPE: PRT
<213> ORGANISM: Marinobacter aqueolei

<400> SEQUENCE: 1

Met Ile Asn Phe Phe Ile Ser Arg Pro Val Phe Ser Trp Val Leu Ala
1               5                   10                  15

Ile Val Ala Met Leu Ala Gly Ile Met Ala Ile Phe Val Leu Pro Val
            20                  25                  30

Gln Arg Tyr Pro Ser Val Ala Pro Pro Ala Val Glu Ile Gln Ala Asp
        35                  40                  45

Tyr Pro Gly Ala Ser Ala Asp Thr Val Ser Asn Thr Val Val Gln Val
    50                  55                  60

Ile Glu Gln Glu Met Thr Gly Leu Asp Asn Leu Leu Tyr Met Gly Ser
65                  70                  75                  80

Thr Ala Asp Ser Ser Gly His Ala Thr Val Thr Leu Thr Phe Ala Ala
                85                  90                  95

Gly Thr Asp Pro Asp Ile Ala Gln Val Gln Val Gln Asn Lys Leu Lys
            100                 105                 110

Leu Ala Glu Pro Arg Leu Pro Glu Val Val Arg Gln Gln Gly Ile Ser
        115                 120                 125

Val Glu Lys Ser Ser Thr Ser Phe Leu Met Val Met Ala Phe Val Ser
    130                 135                 140

Thr Asp Gly Arg Leu Ser Lys Leu Asp Ile Ala Asp Phe Ile Ser Ser
145                 150                 155                 160

Glu Leu Ala Glu Pro Ile Gly Arg Val Thr Gly Ile Gly Ser Val Gln
                165                 170                 175

Val Phe Gly Ser Glu Tyr Ala Met Arg Ile Trp Leu Asp Pro Ser Ala
            180                 185                 190

Leu Thr Asn Tyr Gly Leu Thr Val Ala Asp Val Ser Ala Ala Ile Glu
        195                 200                 205

Ala Gln Asn Ala Gln Val Thr Ala Gly Gln Leu Gly Gly Leu Pro Ala
    210                 215                 220
```

-continued

Val Glu Gly Gln Gln Leu Asn Ala Thr Val Thr Ala Gln Thr Leu Leu
225                 230                 235                 240

Thr Ser Thr Glu Glu Phe Arg Asn Ile Leu Leu Lys Ser Met Pro Asp
            245                 250                 255

Gly Ser Arg Val Arg Leu Gly Asp Val Ala Arg Val Glu Leu Gly Gly
            260                 265                 270

Gly Ala Val Gln Ile Asp Thr Phe Tyr Asp Gly Glu Pro Ala Ala Gly
            275                 280                 285

Leu Gly Ile Asn Leu Ala Pro Gly Ala Asn Ser Leu Ala Val Thr Glu
            290                 295                 300

Ala Val Lys Ala Arg Leu Gln Glu Leu Glu Pro Tyr Phe Pro Glu Gly
305                 310                 315                 320

Val Glu Ile Arg Tyr Pro Tyr Gln Thr Ala Pro Phe Val Glu Ala Ser
                325                 330                 335

Ile Asp Ala Val Val Thr Thr Ile Ile Glu Ala Ile Ala Leu Val Val
            340                 345                 350

Leu Val Met Leu Val Phe Leu Gln Ser Trp Arg Ala Thr Leu Ile Pro
            355                 360                 365

Ala Ile Ala Ile Pro Val Val Leu Leu Gly Thr Phe Ala Ile Met Ala
370                 375                 380

Ala Phe Gly Phe Ser Ile Asn Met Leu Thr Leu Phe Gly Leu Val Leu
385                 390                 395                 400

Ala Ile Gly Leu Leu Val Asp Asp Ala Ile Val Val Glu Asn Val
            405                 410                 415

Glu Arg Val Met His Glu Asp Gly Leu Ser Pro Met Glu Ala Thr Arg
            420                 425                 430

Lys Ser Met Gly Gln Ile Ala Ser Ala Leu Ile Gly Ile Gly Val Val
            435                 440                 445

Leu Ser Ala Val Phe Ile Pro Met Ala Phe Phe Pro Gly Ser Thr Gly
            450                 455                 460

Ala Ile Tyr Arg Gln Phe Ser Leu Ser Ile Ala Gly Ala Met Val Leu
465                 470                 475                 480

Ser Val Leu Val Ala Leu Ile Leu Ser Pro Met Leu Cys Gly Arg Ile
            485                 490                 495

Leu Lys Pro Thr His Glu Arg Thr Leu Leu Gln Lys Leu Phe Gly Trp
            500                 505                 510

Phe Glu Ala Gly Leu Gly Arg Leu Thr Arg Gly Tyr Val Arg Leu Val
            515                 520                 525

Gly His Thr Ala Arg His Ala Trp Leu Tyr Thr Leu Ala Phe Leu Gly
            530                 535                 540

Ile Val Gly Leu Val Ala Val Leu Phe Val Arg Leu Pro Gly Gly Phe
545                 550                 555                 560

Leu Pro Ala Glu Asp Gln Gly Phe Ala Val Val Gln Tyr Gln Leu Pro
            565                 570                 575

Ala Gly Ala Thr Gln Gln Arg Thr Ile Asp Thr Ile Gln Val Ile Glu
            580                 585                 590

Asp Tyr Phe Met Asp Gln Asp Glu Val Gln Gly Leu Phe Thr Ile Ala
            595                 600                 605

Gly Phe Ser Phe Ala Gly Arg Ala Gln Asn Ala Gly Leu Ala Phe Val
            610                 615                 620

Asn Leu Lys Pro Trp Ser Glu Arg Asp Pro Glu Thr Gln Ser Ala Asp
625                 630                 635                 640

Ala Ile Ile Gln Arg Ala Asn Arg Ala Leu Ala Gly Leu Val Arg Asp

```
            645                 650                 655
Gly Arg Ala Phe Ala Phe Asn Leu Pro Pro Ile Pro Glu Leu Gly Gln
        660                 665                 670

Ala Leu Gly Phe Glu Leu Arg Leu Gln Asp Arg Gly Ala Ile Gly His
        675                 680                 685

Glu Ala Leu Met Ala Ala Gln Gly Gln Leu Leu Gln Leu Ala Ala Glu
        690                 695                 700

Ser Pro Val Leu Thr Ser Val Arg Pro Asn Gly Leu Ala Asp Asn Pro
705                 710                 715                 720

Arg Tyr Lys Val Asp Ile Asp Tyr Glu Lys Ala Gln Ala Leu Gly Ile
                725                 730                 735

Glu Pro Ser Glu Ile Ser Arg Leu Leu Ser Val Thr Trp Gly Ser Gln
        740                 745                 750

Tyr Val Asn Asp Phe Leu His Glu Gly Arg Val Lys Arg Val Tyr Val
                755                 760                 765

Gln Gly Asp Ala Pro Phe Arg Met Leu Pro Glu Asp Phe Glu Ala Trp
    770                 775                 780

Tyr Leu Arg Ala Ala Asn Gly Glu Met Thr Pro Leu Ser Glu Val Thr
785                 790                 795                 800

Asn Gly Arg Trp Glu Tyr Gly Ser Pro Arg Leu Glu Arg Phe Asn Gly
                805                 810                 815

Val Pro Ser Arg Gln Ile Gln Gly Glu Pro Ala Pro Gly Tyr Ser Thr
        820                 825                 830

Gly Glu Ala Met Ala Glu Val Glu Arg Leu Ile Ala Gln Leu Pro Asp
        835                 840                 845

Gly Val Ala Gly Ala Trp Ser Gly Leu Ser Tyr Gln Glu Arg Gln Ala
        850                 855                 860

Gly Ala Gln Ala Ser Leu Leu Tyr Ala Leu Ser Ala Leu Val Val Phe
865                 870                 875                 880

Leu Ala Leu Ala Ala Leu Tyr Glu Ser Trp Thr Ile Pro Ile Ser Val
                885                 890                 895

Met Leu Ala Val Pro Leu Gly Val Leu Gly Ala Val Leu Ala Ala Met
        900                 905                 910

Val Arg Gly Leu Pro Asn Asp Val Phe Phe Gln Val Gly Ile Leu Thr
        915                 920                 925

Thr Val Gly Val Thr Ala Arg Asn Ala Ile Leu Leu Val Glu Phe Ala
        930                 935                 940

Arg Ser Leu Glu Asp Gln Gly Met Lys Leu Ile Glu Ala Thr Lys Glu
945                 950                 955                 960

Ala Ala Arg Val Arg Leu Arg Pro Ile Leu Met Thr Ser Val Ala Phe
                965                 970                 975

Gly Met Gly Val Leu Pro Leu Ala Phe Ala Ser Gly Ala Gly Ala Thr
        980                 985                 990

Thr Arg Ile Ala Ile Gly Thr Ala Val Leu Gly Gly Met Ile Ser Ala
        995                 1000                1005

Thr Ile Leu Ala Thr Phe Phe Ile Pro Leu Phe Tyr Val Val Val
        1010                1015                1020

Arg Arg Ile Thr Asp Phe Leu Ser Gly Ser Arg Asp Gln Asp Asp
        1025                1030                1035

Ser Ala Ala Ala Ala Pro Gly Arg Ala Asn Gly Gly Val Ala Asp
        1040                1045                1050

Asp Arg
        1055
```

<210> SEQ ID NO 2
<211> LENGTH: 1041
<212> TYPE: PRT
<213> ORGANISM: Alcanivorax borkumensis

<400> SEQUENCE: 2

```
Met Ala Arg Phe Phe Ile Asp Arg Pro Ile Phe Ala Trp Val Ile Ala
 1               5                  10                  15

Ile Ile Met Met Met Ala Gly Ala Leu Ala Ile Tyr Thr Leu Pro Ile
             20                  25                  30

Glu Gln Tyr Pro Thr Val Ala Pro Pro Gln Val Ser Ile Ala Gly Asn
         35                  40                  45

Tyr Pro Gly Ala Ser Ala Lys Thr Val Glu Asp Ser Val Thr Gln Val
 50                  55                  60

Ile Glu Gln Gln Met Asn Gly Ile Asp Asn Leu Leu Tyr Met Ser Ser
 65                  70                  75                  80

Ser Ser Asp Ser Phe Gly Asn Ala Ala Val Asn Leu Thr Phe Ala Pro
                 85                  90                  95

Gly Thr Asp Pro Asp Ile Ala Gln Val Gln Val Gln Asn Lys Leu Gln
            100                 105                 110

Leu Ala Thr Pro Leu Leu Pro Gln Glu Val Gln Gln Gly Met Gln
            115                 120                 125

Val Thr Lys Ser Ser Asp Ser Phe Leu Met Val Ala Gly Phe Thr Ser
130                 135                 140

Glu Asp Gly Ser Leu Ser Arg Ala Asp Leu Ala Asp Tyr Val Ala Ser
145                 150                 155                 160

Asn Val Gln Asp Pro Val Ser Arg Val Pro Gly Val Gly Gln Ile Gln
                165                 170                 175

Leu Phe Gly Ser Pro Tyr Ala Met Arg Val Trp Leu Asp Pro Asn Lys
            180                 185                 190

Leu Asn Lys Phe Asp Leu Thr Pro Gln Asp Val Thr Gln Thr Ile Glu
            195                 200                 205

Val Gln Asn Asn Gln Val Ala Ser Gly Gln Leu Gly Gly Ala Pro Ala
210                 215                 220

Val Glu Gly Gln Gln Leu Asn Ala Thr Ile Ile Ala Gln Thr Arg Leu
225                 230                 235                 240

Glu Asp Val Asp Gln Phe Glu Asn Ile Leu Leu Lys Val Asn Pro Asp
                245                 250                 255

Gly Ser Arg Val Phe Leu Lys Asp Val Ala Arg Val Glu Leu Ala Ala
            260                 265                 270

Gln Asn Tyr Asp Val Gln Gly Arg Tyr Asn Gly Gln Pro Ala Ala Gly
            275                 280                 285

Leu Ala Ile Ser Leu Ala Thr Gly Ala Asn Ala Leu Asp Thr Ala Glu
            290                 295                 300

Ala Leu Arg Ala Arg Leu Ala Glu Leu Gln Pro Tyr Phe Pro Asp Lys
305                 310                 315                 320

Met Glu Met Val Phe Pro Tyr Asp Thr Thr Pro Phe Val Ser Ile Ser
                325                 330                 335

Ile Glu Glu Val Val His Thr Leu Phe Glu Ala Ile Ile Leu Val Phe
            340                 345                 350

Leu Val Met Tyr Leu Phe Leu Gln Asn Phe Arg Ala Thr Leu Ile Pro
            355                 360                 365

Thr Leu Ala Val Pro Val Val Leu Leu Gly Thr Phe Ala Val Leu Ala
```

370                 375                 380
Ala Phe Gly Phe Ser Ile Asn Thr Leu Thr Met Phe Gly Met Val Leu
385                 390                 395                 400

Ala Ile Gly Leu Leu Val Asp Ala Ile Val Val Glu Asn Val
                405                 410                 415

Glu Arg Val Met His Glu Glu Gly Leu Pro Pro Lys Glu Ala Thr Arg
                420                 425                 430

Lys Ser Met Gly Gln Ile Thr Gly Ala Leu Val Gly Ile Ala Leu Val
                435                 440                 445

Leu Ser Ala Val Phe Val Pro Met Ala Phe Phe Pro Gly Ser Thr Gly
450                 455                 460

Ala Ile Tyr Arg Gln Phe Ser Ile Thr Ile Val Ser Ala Met Val Leu
465                 470                 475                 480

Ser Val Leu Val Ala Leu Ile Leu Thr Pro Ala Leu Cys Ala Thr Met
                485                 490                 495

Leu Lys Ala Lys Asp Ser Glu His Gln Thr Asp His Gly Phe Phe Gly
                500                 505                 510

Trp Phe Asn Arg Thr Phe Asp Lys Ser Ser Arg Arg Tyr Gln Gly Ser
                515                 520                 525

Val Glu Lys Ile Leu Gly Arg Gly Arg Tyr Leu Phe Ile Tyr Val
530                 535                 540

Val Ile Val Gly Val Leu Gly Phe Ser Phe Met Arg Leu Pro Ser Ser
545                 550                 555                 560

Phe Leu Pro Glu Glu Asp Gln Gly Ile Leu Phe Thr Leu Val Thr Leu
                565                 570                 575

Pro Ala Gly Ser Thr Gln Glu Gln Thr Val Lys Val Leu Glu Lys Met
                580                 585                 590

Glu Asp Tyr Tyr Leu Asn Glu Glu Ala Ser Ala Val Asp Gly Leu Phe
                595                 600                 605

Thr Val Ala Gly Phe Ser Phe Thr Gly Arg Gly Gln Asn Ala Gly Met
                610                 615                 620

Ala Phe Val Asn Leu Lys Asp Trp Ser Glu Arg Asp Leu Ser Val Asp
625                 630                 635                 640

Gly Ala Asp Asn Val Val Ala Arg Ala Met Gly Tyr Phe Ser Thr Ile
                645                 650                 655

Arg Glu Ala Met Met Phe Ala Leu Asn Pro Pro Ser Ile Pro Glu Leu
                660                 665                 670

Gly Asn Ala Ser Gly Phe Asp Phe Gln Leu Leu Asp Gln Ser Gly Gln
                675                 680                 685

Gly His Glu Ala Leu Ile Gln Ala Arg Asn Gln Met Leu Gly Met Ala
                690                 695                 700

Ala Gln Asp Pro Arg Leu Ala Gly Val Arg Pro Asn Gly Leu Glu Asp
705                 710                 715                 720

Ser Pro Gln Tyr Gln Ile Asp Ile Asp Gln Gln Lys Ala Lys Ala Leu
                725                 730                 735

Gly Leu Ser Ile Ser Asp Ile Asn Ser Thr Leu Gln Ile Ala Trp Gly
                740                 745                 750

Ser Ser Tyr Val Asn Asn Phe Val Asp Arg Gly Arg Val Lys Arg Val
                755                 760                 765

Tyr Val Gln Ala Asp Ala Pro Tyr Arg Met Leu Pro Glu Asn Val Asn
                770                 775                 780

Asp Trp Phe Val Arg Asn Asn Gln Gly Lys Met Val Pro Phe Ser Thr
785                 790                 795                 800

```
Phe Ala Thr Gly His Trp Thr Tyr Gly Ser Pro Lys Leu Glu Arg Tyr
                805                 810                 815

Asn Gly Val Ser Ser Val Asn Ile Gln Gly Asn Ala Ala Pro Gly Tyr
            820                 825                 830

Ser Thr Gly Asp Ala Met Asp Ala Met Glu Glu Leu Ser Ala Lys Leu
        835                 840                 845

Pro Ala Gly Phe Gly Phe Glu Trp Thr Gly Met Ser Tyr Gln Glu Arg
    850                 855                 860

Gln Ser Gly Asp Gln Ala Pro Ala Leu Tyr Val Ile Ser Leu Leu Val
865                 870                 875                 880

Val Phe Leu Cys Leu Ala Ala Leu Tyr Glu Ser Trp Ser Ile Pro Phe
                885                 890                 895

Ala Val Met Leu Val Val Pro Leu Gly Ile Leu Gly Ala Val Leu Ala
            900                 905                 910

Ala Thr Phe Arg Asp Leu Asn Asn Asp Val Phe Phe Gln Val Gly Leu
        915                 920                 925

Leu Thr Thr Ile Gly Leu Ser Ala Lys Asn Ala Ile Leu Ile Ala Glu
    930                 935                 940

Phe Ala Leu Glu Leu Glu Gln Lys Gly Glu His Leu Leu Lys Ala Thr
945                 950                 955                 960

Leu Glu Ala Val Arg Met Arg Leu Arg Pro Ile Leu Met Thr Ser Leu
                965                 970                 975

Ala Phe Met Leu Gly Val Thr Pro Leu Met Ile Ser Thr Gly Ala Gly
            980                 985                 990

Ala Gly Ala Arg Asn Ala Ile Gly Thr Gly Val Phe Gly Gly Met Leu
        995                 1000                1005

Thr Ala Thr Val Leu Ala Ile Phe Phe Ile Pro Leu Phe Tyr Val
    1010                1015                1020

Ala Val Arg Lys Leu Ser Val Pro Leu Asp Gly Lys Lys Lys
    1025                1030                1035

Gly Lys Glu
    1040

<210> SEQ ID NO 3
<211> LENGTH: 1042
<212> TYPE: PRT
<213> ORGANISM: Pseudomonas putida

<400> SEQUENCE: 3

Met Pro Gln Phe Phe Ile Asp Arg Pro Val Phe Ala Trp Val Val Ala
1               5                   10                  15

Leu Phe Ile Leu Leu Ala Gly Ala Leu Ala Ile Pro Gln Leu Pro Val
            20                  25                  30

Ala Gln Tyr Pro Asn Val Ala Pro Pro Gln Val Glu Ile Tyr Ala Val
        35                  40                  45

Tyr Pro Gly Ala Ser Ala Ala Thr Met Asp Glu Ser Val Val Ser Leu
    50                  55                  60

Ile Glu Gln Glu Leu Asn Gly Ala Asp Asn Leu Leu Tyr Phe Glu Ser
65                  70                  75                  80

Gln Ser Ser Leu Gly Ser Ala Thr Ile Thr Ala Thr Phe Ala Pro Gly
                85                  90                  95

Thr His Pro Asp Leu Ala Gln Val Asp Val Gln Asn Arg Leu Lys Val
            100                 105                 110

Val Glu Ser Arg Leu Pro Arg Pro Val Thr Gln Gln Gly Leu Gln Val
```

-continued

```
            115                 120                 125
Glu Lys Val Ser Thr Gly Phe Leu Leu Ala Thr Leu Thr Ser Glu
        130                 135                 140
Asp Gly Lys Leu Asp Glu Thr Ala Leu Ser Asp Ile Leu Ala Arg Asn
145                 150                 155                 160
Val Met Asp Glu Ile Arg Arg Leu Lys Gly Val Gly Lys Ala Gln Leu
                165                 170                 175
Tyr Gly Ser Glu Arg Ala Met Arg Ile Trp Ile Asp Pro Arg Lys Leu
            180                 185                 190
Ile Gly Phe Asn Leu Thr Pro Asn Asp Val Ala Glu Ala Ile Ala Ala
            195                 200                 205
Gln Asn Ala Gln Val Ala Pro Gly Ser Ile Gly Asp Leu Pro Ser Arg
210                 215                 220
Ser Thr Gln Glu Ile Thr Ala Asn Val Val Lys Gly Gln Leu Ser
225                 230                 235                 240
Ser Pro Asp Glu Phe Ala Ala Ile Val Leu Arg Ala Asn Pro Asp Gly
                245                 250                 255
Ser Thr Val Thr Ile Gly Asp Val Ala Arg Val Glu Ile Gly Ala Gln
            260                 265                 270
Glu Tyr Gln Tyr Gly Thr Arg Leu Asn Gly Lys Pro Ala Thr Ala Phe
        275                 280                 285
Ser Val Gln Leu Ser Pro Gly Ala Asn Ala Met Glu Thr Ala Thr Leu
290                 295                 300
Val Arg Ala Lys Met Gln Asp Leu Ala Arg Tyr Phe Pro Glu Gly Val
305                 310                 315                 320
Lys Tyr Asp Ile Pro Tyr Asp Thr Ser Pro Phe Val Lys Val Ser Ile
                325                 330                 335
Glu Gln Val Ile Asn Thr Leu Phe Glu Ala Met Leu Val Phe Ala
            340                 345                 350
Val Met Phe Leu Phe Leu Gln Asn Leu Arg Tyr Thr Leu Ile Pro Thr
        355                 360                 365
Leu Val Val Pro Val Ala Leu Met Gly Thr Phe Ala Val Met Leu Ala
370                 375                 380
Met Gly Phe Ser Val Asn Val Leu Thr Leu Phe Gly Met Val Leu Ala
385                 390                 395                 400
Ile Gly Ile Leu Val Asp Asp Ala Ile Val Val Glu Asn Val Glu
                405                 410                 415
Arg Ile Met Ala Glu Glu Gly Leu Pro Pro Lys Gln Ala Thr Arg Lys
            420                 425                 430
Ala Met Gly Gln Ile Ser Gly Ala Ile Val Gly Ile Thr Leu Val Leu
        435                 440                 445
Val Ala Val Phe Leu Pro Met Ala Phe Met Gln Gly Ser Val Gly Val
450                 455                 460
Ile Tyr Gln Gln Phe Ser Leu Ser Met Ala Val Ser Ile Leu Phe Ser
465                 470                 475                 480
Ala Phe Leu Ala Leu Ser Leu Thr Pro Ala Leu Cys Ala Thr Leu Leu
                485                 490                 495
Lys Pro Val Ala Lys Gly Glu His His Glu Arg Lys Gly Phe Phe Gly
            500                 505                 510
Trp Phe Asn Arg Arg Phe Glu Ser Met Ser Asn Gly Tyr Gln Arg Trp
        515                 520                 525
Val Val Gln Ala Leu Lys Arg Ser Gly Arg Tyr Leu Leu Val Tyr Ala
530                 535                 540
```

```
Val Leu Leu Ala Val Leu Gly Tyr Gly Phe Ser Gln Leu Pro Thr Ala
545                 550                 555                 560

Phe Leu Pro Thr Glu Asp Gln Gly Tyr Thr Ile Thr Asp Ile Gln Leu
                565                 570                 575

Pro Pro Gly Ala Ser Arg Met Arg Thr Glu Gln Val Ala Ala Gln Ile
            580                 585                 590

Glu Ala His Asn Ala Glu Glu Pro Gly Val Gly Asn Thr Thr Leu Ile
        595                 600                 605

Leu Gly Phe Ser Phe Ser Gly Ser Gly Gln Asn Ala Ala Leu Ala Phe
    610                 615                 620

Thr Thr Leu Lys Asp Trp Ser Glu Arg Gly Ala Asp Asp Ser Ala Gln
625                 630                 635                 640

Ser Ile Ala Asp Arg Ala Thr Met Ala Phe Thr Gln Leu Lys Asp Ala
                645                 650                 655

Ile Ala Tyr Ser Val Leu Pro Pro Ile Asp Gly Leu Gly Glu Ser
            660                 665                 670

Thr Gly Phe Glu Phe Arg Leu Gln Asp Arg Gly Gly Met Gly His Ala
        675                 680                 685

Glu Leu Met Ala Ala Arg Asp Gln Leu Leu Glu Ser Ala Ser Lys Ser
    690                 695                 700

Lys Val Leu Thr Asn Val Arg Glu Ala Ser Leu Ala Glu Ser Pro Gln
705                 710                 715                 720

Val Gln Leu Glu Ile Asp Arg Arg Gln Ala Asn Ala Leu Gly Val Ser
                725                 730                 735

Phe Ala Asp Ile Gly Thr Val Leu Asp Val Ala Val Gly Ser Ser Tyr
            740                 745                 750

Val Asn Asp Phe Pro Asn Gln Gly Arg Met Gln Arg Val Val Gln
        755                 760                 765

Ala Glu Gly Asp Gln Arg Ser Gln Val Glu Asp Leu Leu Asn Ile His
    770                 775                 780

Val Arg Asn Asp Ser Gly Lys Met Val Pro Leu Gly Ala Phe Val Gln
785                 790                 795                 800

Ala Arg Trp Val Ser Gly Pro Val Gln Leu Thr Arg Tyr Asn Gly Tyr
                805                 810                 815

Pro Ala Val Ser Ile Ser Gly Glu Pro Ala Ala Gly Tyr Ser Ser Gly
            820                 825                 830

Glu Ala Met Ala Glu Val Glu Arg Leu Val Ala Gln Leu Pro Ala Gly
        835                 840                 845

Thr Gly Leu Glu Trp Thr Gly Leu Ser Leu Gln Glu Arg Leu Ser Gly
    850                 855                 860

Ser Gln Ala Pro Leu Leu Met Ala Leu Ser Leu Leu Val Phe Leu
865                 870                 875                 880

Cys Leu Ala Ala Leu Tyr Glu Ser Trp Ser Ile Pro Thr Ala Val Leu
                885                 890                 895

Leu Val Val Pro Leu Gly Val Leu Gly Ala Val Leu Ala Val Thr Leu
            900                 905                 910

Arg Gly Met Pro Asn Asp Val Phe Phe Lys Val Gly Leu Ile Thr Leu
        915                 920                 925

Ile Gly Leu Ser Ala Lys Asn Ala Ile Leu Ile Ile Glu Phe Ala Lys
    930                 935                 940

His Leu Val Asp Gln Gly Val Asp Ala Ala Asp Ala Ala Val Gln Ala
945                 950                 955                 960
```

```
Ala Arg Leu Arg Leu Arg Pro Ile Val Met Thr Ser Leu Ala Phe Ile
            965                 970                 975

Leu Gly Val Val Pro Leu Ala Ile Ala Ser Gly Ala Ser Ser Ala Ser
        980                 985                 990

Gln Gln Ala Ile Gly Thr Gly Val Ile Gly Gly Met Leu Ser Ala Thr
        995                1000                1005

Leu Ala Val Val Phe Val Pro Val Phe Phe Val Val Met Arg
       1010                1015                1020

Leu Ser Gly Arg Arg Gln Ala His Asp Ser Asp Gly Gln Pro Val
       1025                1030                1035

Pro Arg Glu Ser
       1040

<210> SEQ ID NO 4
<211> LENGTH: 1045
<212> TYPE: PRT
<213> ORGANISM: Pseudomonas aeruginosa

<400> SEQUENCE: 4

Met Ala Arg Phe Phe Ile Asp Arg Pro Val Phe Ala Trp Val Ile Ser
1               5                  10                  15

Leu Leu Ile Val Leu Ala Gly Val Leu Ala Ile Arg Phe Leu Pro Val
                20                  25                  30

Ala Gln Tyr Pro Asp Ile Ala Pro Pro Val Val Asn Val Ser Ala Ser
            35                  40                  45

Tyr Pro Gly Ala Ser Ala Lys Val Val Glu Ala Val Thr Ala Ile
        50                  55                  60

Ile Glu Arg Glu Met Asn Gly Ala Pro Gly Leu Leu Tyr Thr Lys Ala
65                  70                  75                  80

Thr Ser Ser Thr Gly Gln Ala Ser Leu Thr Leu Thr Phe Arg Gln Gly
                85                  90                  95

Val Asn Ala Asp Leu Ala Ala Val Glu Val Gln Asn Arg Leu Lys Ile
            100                 105                 110

Val Glu Ser Arg Leu Pro Glu Ser Val Arg Arg Asp Gly Ile Tyr Val
        115                 120                 125

Glu Lys Ala Ala Asp Ser Ile Gln Leu Ile Val Thr Leu Thr Ser Ser
130                 135                 140

Ser Gly Arg Tyr Asp Ala Met Glu Leu Gly Glu Ile Ala Ser Ser Asn
145                 150                 155                 160

Val Leu Gln Ala Leu Arg Arg Val Glu Gly Val Gly Lys Val Glu Thr
                165                 170                 175

Trp Gly Ala Glu Tyr Ala Met Arg Ile Trp Pro Asp Pro Ala Lys Leu
            180                 185                 190

Thr Ser Met Asn Leu Ser Ala Ser Asp Leu Val Asn Ala Val Arg Arg
        195                 200                 205

His Asn Ala Arg Leu Thr Val Gly Asp Ile Gly Asn Leu Gly Val Pro
    210                 215                 220

Asp Ser Ala Pro Ile Ser Ala Thr Val Lys Val Asp Asp Thr Leu Val
225                 230                 235                 240

Thr Pro Glu Gln Phe Gly Glu Ile Pro Leu Arg Ile Arg Ala Asp Gly
                245                 250                 255

Gly Ala Ile Arg Leu Arg Asp Val Ala Arg Val Glu Phe Gly Gln Ser
            260                 265                 270

Glu Tyr Gly Phe Val Ser Arg Val Asn Gln Met Thr Ala Thr Gly Leu
        275                 280                 285
```

```
Ala Val Lys Met Ala Pro Gly Ser Asn Ala Val Ala Thr Ala Lys Arg
        290                 295                 300

Ile Arg Ala Thr Leu Asp Glu Leu Ser Arg Tyr Phe Pro Glu Gly Val
305                 310                 315                 320

Ser Tyr Asn Ile Pro Tyr Asp Thr Ser Ala Phe Val Glu Ile Ser Ile
                325                 330                 335

Arg Lys Val Val Ser Thr Leu Leu Glu Ala Met Leu Leu Val Phe Ala
                340                 345                 350

Val Met Tyr Leu Phe Met Gln Asn Phe Arg Ala Thr Leu Ile Pro Thr
        355                 360                 365

Leu Val Val Pro Val Ala Leu Leu Gly Thr Phe Thr Val Met Leu Gly
370                 375                 380

Leu Gly Phe Ser Ile Asn Val Leu Thr Met Phe Gly Met Val Leu Ala
385                 390                 395                 400

Ile Gly Ile Leu Val Asp Asp Ala Ile Ile Val Val Glu Asn Val Glu
                405                 410                 415

Arg Leu Met Ala Glu Glu Gly Leu Ser Pro His Asp Ala Thr Val Lys
                420                 425                 430

Ala Met Arg Gln Ile Ser Gly Ala Ile Val Gly Ile Thr Val Val Leu
        435                 440                 445

Val Ser Val Phe Val Pro Met Ala Phe Phe Ser Gly Ala Val Gly Asn
450                 455                 460

Ile Tyr Arg Gln Phe Ala Val Thr Leu Ala Val Ser Ile Gly Phe Ser
465                 470                 475                 480

Ala Phe Leu Ala Leu Ser Leu Thr Pro Ala Leu Cys Ala Thr Leu Leu
                485                 490                 495

Arg Pro Ile Asp Ala Asp His His Glu Lys Arg Gly Phe Phe Gly Trp
                500                 505                 510

Phe Asn Arg Ala Phe Leu Arg Leu Thr Gly Arg Tyr Arg Asn Ala Val
        515                 520                 525

Ala Gly Ile Leu Ala Arg Pro Ile Arg Trp Met Leu Val Tyr Thr Leu
530                 535                 540

Val Ile Gly Val Val Ala Leu Leu Phe Val Arg Leu Pro Gln Ala Phe
545                 550                 555                 560

Leu Pro Glu Glu Asp Gln Gly Asp Phe Met Ile Met Val Met Gln Pro
                565                 570                 575

Glu Gly Thr Pro Met Ala Glu Thr Met Ala Asn Val Gly Asp Val Glu
                580                 585                 590

Arg Tyr Leu Ala Glu His Glu Pro Val Ala Tyr Ala Val Gly
        595                 600                 605

Gly Phe Ser Leu Tyr Gly Asp Gly Thr Ser Ser Ala Met Ile Phe Ala
        610                 615                 620

Thr Leu Lys Asp Trp Ser Glu Arg Glu Ala Ser Gln His Val Gly
625                 630                 635                 640

Ala Ile Val Glu Arg Ile Asn Gln Arg Phe Ala Gly Leu Pro Asn Arg
                645                 650                 655

Thr Val Tyr Ala Met Asn Ser Pro Pro Leu Pro Asp Leu Gly Ser Thr
                660                 665                 670

Ser Gly Phe Asp Phe Arg Leu Gln Asp Arg Gly Gly Val Gly Tyr Glu
        675                 680                 685

Ala Leu Val Lys Ala Arg Asp Gln Leu Leu Ala Arg Ala Ala Glu Asp
690                 695                 700
```

Pro Arg Leu Ala Asn Val Met Phe Ala Gly Gln Gly Glu Ala Pro Gln
705                 710                 715                 720

Ile Arg Leu Asp Ile Asp Arg Arg Lys Ala Glu Thr Leu Gly Val Ser
            725                 730                 735

Met Asp Glu Ile Asn Thr Thr Leu Ala Val Met Phe Gly Ser Asp Tyr
        740                 745                 750

Ile Gly Asp Phe Met His Gly Ser Gln Val Arg Lys Val Val Val Gln
            755                 760                 765

Ala Asp Gly Ala Lys Arg Leu Gly Ile Asp Asp Ile Gly Arg Leu His
770                 775                 780

Val Arg Asn Glu Gln Gly Glu Met Val Pro Leu Ala Thr Phe Ala Lys
785                 790                 795                 800

Ala Ala Trp Thr Leu Gly Pro Pro Gln Leu Thr Arg Tyr Asn Gly Tyr
            805                 810                 815

Pro Ser Phe Asn Leu Glu Gly Gln Ala Ala Pro Gly Tyr Ser Ser Gly
        820                 825                 830

Glu Ala Met Gln Ala Met Glu Gln Leu Met Gln Gly Leu Pro Glu Gly
            835                 840                 845

Ile Ala His Glu Trp Ser Gly Gln Ser Phe Glu Glu Arg Leu Ser Gly
850                 855                 860

Ala Gln Ala Pro Ala Leu Phe Ala Leu Ser Val Leu Ile Val Phe Leu
865                 870                 875                 880

Ala Leu Ala Ala Leu Tyr Glu Ser Trp Ser Ile Pro Leu Ala Val Ile
            885                 890                 895

Leu Val Val Pro Leu Gly Val Leu Gly Ala Leu Leu Gly Val Ser Leu
        900                 905                 910

Arg Gly Leu Pro Asn Asp Ile Tyr Phe Lys Val Gly Leu Ile Thr Ile
            915                 920                 925

Ile Gly Leu Ser Ala Lys Asn Ala Ile Leu Ile Ile Glu Val Ala Lys
930                 935                 940

Asp His Tyr Gln Glu Gly Met Ser Leu Leu Gln Ala Thr Leu Glu Ala
945                 950                 955                 960

Ala Arg Leu Arg Leu Arg Pro Ile Val Met Thr Ser Leu Ala Phe Gly
            965                 970                 975

Phe Gly Val Val Pro Leu Ala Leu Ser Ser Gly Ala Gly Ser Gly Ala
        980                 985                 990

Gln Val Ala Ile Gly Thr Gly Val Leu Gly Gly Ile Val Thr Ala Thr
            995                 1000                1005

Val Leu Ala Val Phe Leu Val Pro Leu Phe Phe Leu Val Val Gly
    1010                1015                1020

Arg Leu Phe Arg Leu Arg Lys Ala Pro Arg Thr Gly Asn Ser Pro
    1025                1030                1035

Gln Ile Pro Thr Glu Gln Ala
    1040                1045

<210> SEQ ID NO 5
<211> LENGTH: 1036
<212> TYPE: PRT
<213> ORGANISM: Marinobacter aqueolei

<400> SEQUENCE: 5

Met Pro Arg Phe Phe Ile Glu Arg Pro Ile Phe Ala Trp Val Val Ala
1               5                   10                  15

Leu Met Leu Met Leu Gly Gly Gly Leu Ala Val Lys Asn Leu Ala Val
                20                  25                  30

-continued

```
Asn Gln Phe Pro Asp Val Ala Pro Ala Ile Ala Leu Ser Val Asn
         35                  40                  45
Tyr Pro Gly Ala Ser Ala Gln Thr Val Gln Asp Thr Val Val Gln Val
 50                  55                  60
Ile Glu Gln Gln Leu Asn Gly Leu Asp Gly Leu Arg Tyr Ile Ser Ser
 65                  70                  75                  80
Glu Ser Asn Ser Asp Gly Ser Met Thr Ile Ala Thr Phe Glu Gln
                 85                  90                  95
Gly Thr Asp Pro Asp Ile Ala Gln Val Gln Val Gln Asn Lys Leu Gln
                100                 105                 110
Leu Ala Asn Pro Leu Leu Pro Glu Glu Val Gln Arg Gln Gly Ile Arg
                115                 120                 125
Val Ser Lys Tyr Lys Val Asn Phe Phe Thr Val Phe Ala Leu Thr Ser
                130                 135                 140
Pro Asp Gly Lys Tyr Thr Gln Gly Asp Leu Ala Asp Tyr Ile Val Ser
145                 150                 155                 160
Asn Ile Gln Asp Pro Val Ala Arg Thr Gln Gly Val Gly Asp Phe Leu
                165                 170                 175
Leu Phe Gly Ser Gln Tyr Ala Met Arg Leu Trp Leu Asp Pro Glu Lys
                180                 185                 190
Leu Asn Ser Tyr Gln Leu Thr Pro Gln Asp Val Ile Asn Ser Val Arg
                195                 200                 205
Ala Gln Asn Val Gln Val Ser Ala Gly Gln Leu Gly Gly Leu Pro Thr
                210                 215                 220
Ala Glu Gly Val Gln Leu Gln Ala Thr Val Ile Gly Lys Gln Arg Met
225                 230                 235                 240
Lys Thr Ala Glu Glu Phe Glu Asn Ile Leu Leu Lys Val Asn Pro Asp
                245                 250                 255
Gly Ser Gln Val Arg Leu Ala Asp Val Ala Glu Val Asn Leu Gly Asn
                260                 265                 270
Glu Asn Tyr Ala Thr Thr Gly Lys Tyr Asn Gly Ala Pro Ala Ala Gly
                275                 280                 285
Met Ala Leu Arg Leu Ala Thr Gly Ala Asn Gln Leu Glu Thr Ala Gly
                290                 295                 300
Arg Val Lys Glu Thr Leu Ala Glu Leu Glu Arg Phe Leu Pro Glu Gly
305                 310                 315                 320
Val Glu Ile Val Phe Pro Tyr Asp Thr Thr Pro Val Val Ser Ala Ser
                325                 330                 335
Ile Glu Thr Val Ala Met Thr Leu Ile Glu Ala Val Val Leu Val Phe
                340                 345                 350
Leu Val Met Phe Leu Phe Leu Gln Ser Trp Arg Ala Thr Ile Ile Pro
                355                 360                 365
Thr Leu Ala Val Pro Val Val Leu Leu Ala Thr Phe Gly Val Leu Tyr
370                 375                 380
Ala Phe Gly Phe Thr Val Asn Val Met Thr Met Phe Ala Met Val Leu
385                 390                 395                 400
Ala Ile Gly Leu Leu Val Asp Asp Ala Ile Val Val Glu Asn Val
                405                 410                 415
Glu Arg Leu Met Glu Glu Gly Leu Ser Pro Lys Glu Ala Ala Lys
                420                 425                 430
Lys Ser Met Asp Gln Ile Ser Gly Ala Leu Leu Gly Ile Gly Leu Val
                435                 440                 445
```

-continued

```
Ile Ser Ala Val Phe Leu Pro Met Ala Phe Gly Gly Ser Thr Gly
450                 455                 460

Val Ile Tyr Arg Gln Phe Ser Val Thr Ile Ile Ser Ala Met Ser Phe
465                 470                 475                 480

Ser Val Leu Val Ala Phe Ile Phe Thr Pro Ala Leu Cys Ala Thr Leu
            485                 490                 495

Leu Lys Pro Gly Asp Gln His Val Arg Lys Gly Phe Phe Gly Trp Phe
        500                 505                 510

Asn Arg Thr Phe Asp Arg Ser Ala Asp Arg Tyr Lys Ser Gly Val Ser
        515                 520                 525

Tyr Leu Ile Lys Arg Lys Gly Arg Phe Met Gly Val Tyr Leu Leu Leu
530                 535                 540

Val Val Ala Val Gly Phe Leu Phe Lys Gly Leu Pro Thr Ala Phe Leu
545                 550                 555                 560

Pro Asp Glu Asp Gln Gly Val Met Ile Val Met Val Gln Leu Pro Thr
                565                 570                 575

Asn Ala Thr Gly Glu Arg Thr Glu Ala Val Leu Ala Glu Ala Gly Asn
            580                 585                 590

Tyr Leu Leu Glu Glu Glu Ser Glu Val Val Lys Ser Val Met Ser Val
    595                 600                 605

Arg Gly Phe Asn Phe Ala Gly Arg Gly Gln Asn Ser Gly Ile Leu Phe
        610                 615                 620

Val Asp Leu Lys Pro Phe Ala Asp Arg Glu Ser Phe Ala Gln Ser Val
625                 630                 635                 640

Phe Ala Leu Ala Gly Arg Ser Gly Ala Arg Phe Ala Gln Ile Lys Asp
                645                 650                 655

Ala Ile Val Phe Pro Ile Val Pro Pro Ala Ile Leu Glu Leu Gly Asn
            660                 665                 670

Ala Thr Gly Phe Asp Leu Tyr Leu Lys Asp Asn Gly Ala Ile Gly His
        675                 680                 685

His Ala Leu Met Ala Ala Thr Asn Glu Phe Ile Ser Arg Ala Asn Ala
    690                 695                 700

Ala Pro Glu Leu Asn Met Val Arg His Asn Gly Leu Pro Asp Glu Pro
705                 710                 715                 720

Gln Tyr Gln Val Ile Ile Asp Asp Glu Lys Ala Arg Leu Leu Gln Val
                725                 730                 735

Ser Ile Ala Asp Ile Asn Ala Thr Met Ser Ala Ala Trp Gly Ser Ser
            740                 745                 750

Tyr Val Asn Asp Phe Leu His Asn Gly Arg Val Lys Lys Val Tyr Val
        755                 760                 765

Gln Gly Lys Pro Asp Ser Arg Leu Ala Pro Glu Asp Phe Asp Lys Trp
    770                 775                 780

Phe Val Arg Asn Ala Gln Gly Glu Met Val Pro Phe Ala Ala Phe Ala
785                 790                 795                 800

Thr Gly Glu Trp Val Phe Gly Ser Pro Arg Leu Gln Arg Tyr Gln Gly
                805                 810                 815

Leu Pro Ala Thr Gln Ile Gln Gly Ala Pro Ala Asn Gly Tyr Ser Thr
            820                 825                 830

Gly Asp Ala Met Ala Ala Leu Glu Arg Ile Ala Ala Asp Leu Pro Gln
        835                 840                 845

Gly Leu Gly Leu Glu Tyr Thr Gly Leu Ser Phe Glu Glu Lys Gln Ala
    850                 855                 860

Gly Asn Gln Ala Met Met Leu Tyr Leu Leu Ser Ile Leu Val Val Phe
```

```
                865                 870                 875                 880
Leu Cys Leu Ala Ala Leu Tyr Glu Ser Trp Ser Ile Pro Phe Ala Val
                    885                 890                 895

Ile Met Leu Val Pro Leu Gly Val Leu Gly Ala Val Leu Ala Thr Met
            900                 905                 910

Ala Arg Gly Leu Ser Asn Asp Val Phe Phe Gln Val Gly Met Leu Thr
        915                 920                 925

Thr Met Gly Leu Ala Ala Lys Asn Ala Ile Leu Ile Val Glu Phe Ala
    930                 935                 940

Arg Gln Leu Tyr Glu Gln Glu Gly Lys Pro Leu Leu Gln Ala Thr Ala
945                 950                 955                 960

Glu Ala Ala Arg Leu Arg Leu Arg Pro Ile Ile Met Thr Ser Leu Ala
                965                 970                 975

Phe Ile Phe Gly Val Leu Pro Met Ala Ile Ala Ser Gly Ala Ser Ser
            980                 985                 990

Ala Ser Gln His Ala Ile Gly Thr Ala Val Val Gly Gly Thr Leu Ala
        995                 1000                1005

Ala Thr Ile Leu Ala Ile Phe Phe Val Pro Leu Phe Tyr Val Phe
    1010                1015                1020

Val Val Gly Leu Thr Gly Lys Arg Lys Ser Ala Asp Asp
    1025                1030                1035

<210> SEQ ID NO 6
<211> LENGTH: 51
<212> TYPE: DNA
<213> ORGANISM: Artificial Sequence
<220> FEATURE:
<223> OTHER INFORMATION: Strain and plasmid construction: second PCR
      reaction reverse primer

<400> SEQUENCE: 6
gcctggagat ccttactcga gtttggatcc tcagtggtga tggtgatgat g           51

<210> SEQ ID NO 7
<211> LENGTH: 30
<212> TYPE: DNA
<213> ORGANISM: Artificial Sequence
<220> FEATURE:
<223> OTHER INFORMATION: Strain and plasmid construction: second PCR
      reaction forward primer

<400> SEQUENCE: 7
caaaagatct tttaagaagg agatatacat                                    30
```

MODIFIED HOST CELLS WITH EFFLUX PUMPS

CROSS-REFERENCE TO RELATED APPLICATIONS

This application claims priority to U.S. Provisional Patent Application Ser. No. 61/348,201, filed May 25, 2010, which is hereby incorporated by reference in its entirety.

STATEMENT OF GOVERNMENTAL SUPPORT

The invention described and claimed herein was made in part utilizing funds supplied by the U.S. Department of Energy under Contract No. DE-AC02-05CH11231. The government has certain rights in this invention.

FIELD OF THE INVENTION

This invention relates generally to modified host cells with efflux pumps.

BACKGROUND OF THE INVENTION

Cellulosic biofuel production aims to use microbes to convert sugars derived from plant matter into compounds like alcohols, alkenes, or cyclic hydrocarbons [3-5]. However, many biofuels are inherently toxic to microorganisms, limiting production potential. Microbial systems have several native strategies for dealing with fuel toxicity [2]. Some mechanisms, such as reducing membrane permeability or metabolizing hydrocarbons, are not ideal in a production strain because they may hinder endogenous biofuel production. A promising alternative uses membrane transport proteins to export biofuel [6].

Microbial metabolic pathways can be used to produce a variety of compounds that can serve as biofuels. Short to mid-length chain (C4-C12) alcohols such as butanol, isopentanol, and geraniol are bio-gasoline candidates [1, 3]. Longer chain compounds (C9-C23) such as geranyl acetate and farnesyl hexanoate are bio-diesel alternatives. In addition, cyclic alkenes like limonene and pinene serve as precursors to bio-jet fuel [1, 7]. While microbial biosynthetic routes to most of these compounds exist, these compounds have known antimicrobial activity.

Efflux pumps are secondary transporters that can export toxins from the cell using the proton motive force [8-10]. In gram-negative bacteria they are composed of three protein homotrimers: an inner membrane protein—the proton antiporter that is responsible for substrate recognition, a periplasmic linker protein, and an outer membrane channel. All three proteins are essential for function and the corresponding genes are commonly arranged together in an operon.

A small number of efflux pumps have been previously characterized as solvent-resistant. Examples include ttgABC, ttgDEF, ttgGHI (toluene tolerance genes) [11, 12] and srpABC (solvent resistance pump) [13] from *Pseudomonas putida*. These pumps are induced by a range of compounds [14], but appear to be fairly specific to solvents [14, 15]. In addition, multidrug efflux pumps, like mexAB-oprM, mexCD-oprJ, and mexEF-oprN from *Pseudomonas aeruginosa* [16] and acrAB-tolC from *E. coli* [17], export a very broad range of substrates, including solvents. All efflux pumps in gram negative bacteria that have been characterized as solvent resistant fall into the hydrophobe/amphiphile efflux (HAE1) family of resistance-nodulation-division (RND) efflux pumps [18]; members of this family export a particularly wide range of toxic substrates, though not all pumps in this class export solvents [17]. Sequenced bacterial genomes encode a large number of HAE1 efflux pumps, and present a largely unexplored resource for discovering novel pumps with potential for use in engineering fuel tolerance.

SUMMARY OF THE INVENTION

The present invention provides for a modified host cell comprising a heterologous expression of an efflux pump capable of transporting an organic molecule out of the host cell wherein the organic molecule at a sufficiently high concentration inhibits or reduces the growth rate of or is lethal to the host cell. "Heterologous expression" means either (1) the efflux pump is native to the host cell but is expressed, under certain desired conditions, at a level of expression that is higher than the native expression of the efflux pump, or (2) the efflux pump is heterologous to the host cell. The "certain desired conditions" include, but are not limited to, conditions, such as environmental conditions, where the organic molecule is maximally or substantially produced by the host cell.

The present invention provides for a method for culturing or growing the modified host cell of the present invention, comprising: (a) providing a modified host cell of the present invention in a solution, and (b) culturing or growing the modified host cell such that the efflux pump is expressed, such that the modified host cell has a growth rate or doubling time that is faster compared to the growth rate or doubling time of a cell identical to the modified host cell except that the cell does not express the efflux pump.

In some embodiments of the invention, the culturing or growing step (b) comprises culturing or growing the host cell in an environment comprising a sufficiently high concentration of the organic molecule such that the organic molecule inhibits or reduces the growth rate of or is lethal to the host cell. In some embodiments of the invention, the method further comprises: (c) separating the organic molecule produced by the host cell, and pumped out of the host cell, from the host cell. In some embodiments of the invention, the separating step (c) can comprise carrying out procedure(s) well known to one skilled in the art including, but not limited to, separating the liquid portion of the solution from the host cells in the solution.

BRIEF DESCRIPTION OF THE DRAWINGS

The foregoing aspects and others will be readily appreciated by the skilled artisan from the following description of illustrative embodiments when read in conjunction with the accompanying drawings.

The third column of plots shows the final cell densities ($N_i$ at 72 hours) plotted versus $d_i$. These data show that final $N_i$ values correlate well with growth rate. In other words, the higher ranked pumps are better at improving growth.

Figure 6:
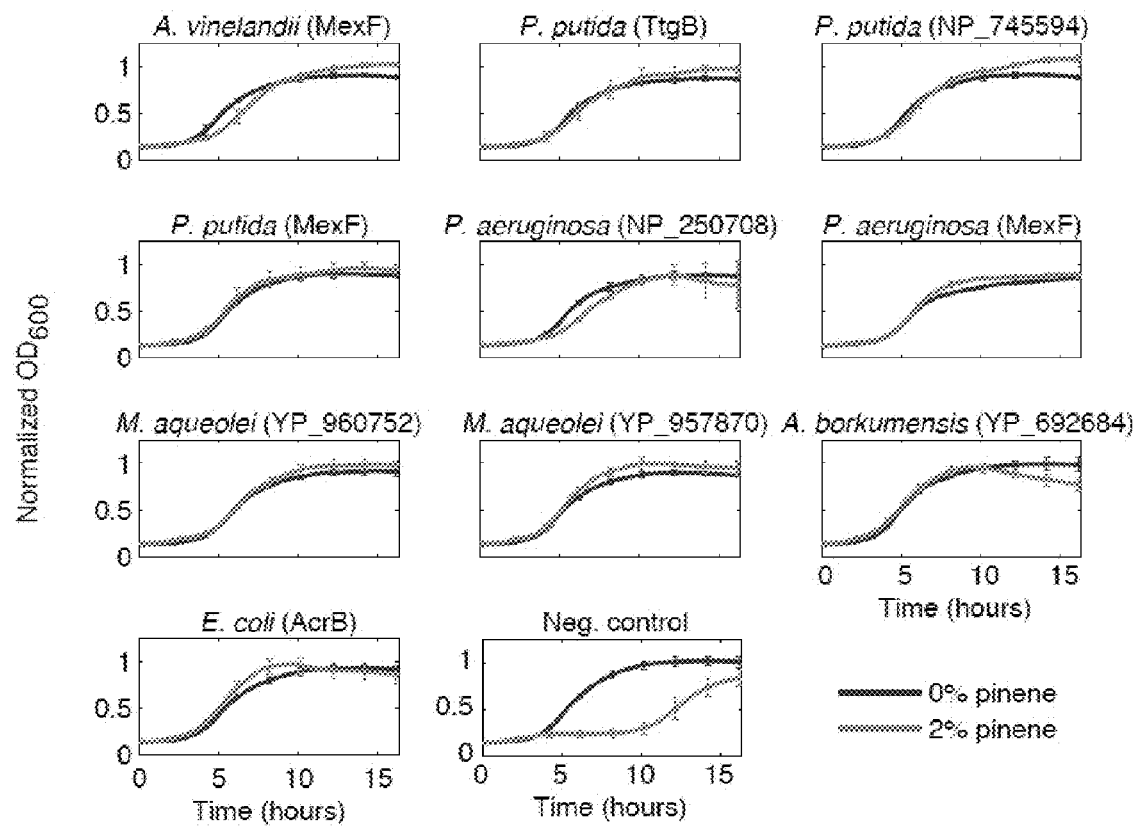

FIG. 6 shows growth curves of α-pinene competition winners versus time. Green line is growth with 2% α-pinene, blue line is without. All data are normalized to the final cell density of the negative control strain grown with 0% α-pinene. Data show that all competition winners are resistant to α-pinene.

Figure 7:
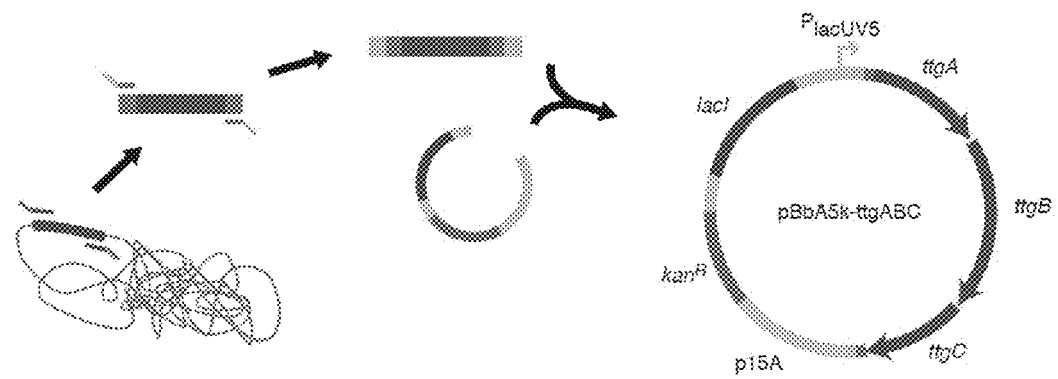

FIG. 7 shows the library cloning strategy and plasmid map. The two-stage PCR adds short linker sequences onto the efflux pump insert which are used in subsequent annealing steps (Supporting Methods in Example 1). The plasmid on the right is an example of one of the completed efflux pump library members.

Figure 8:
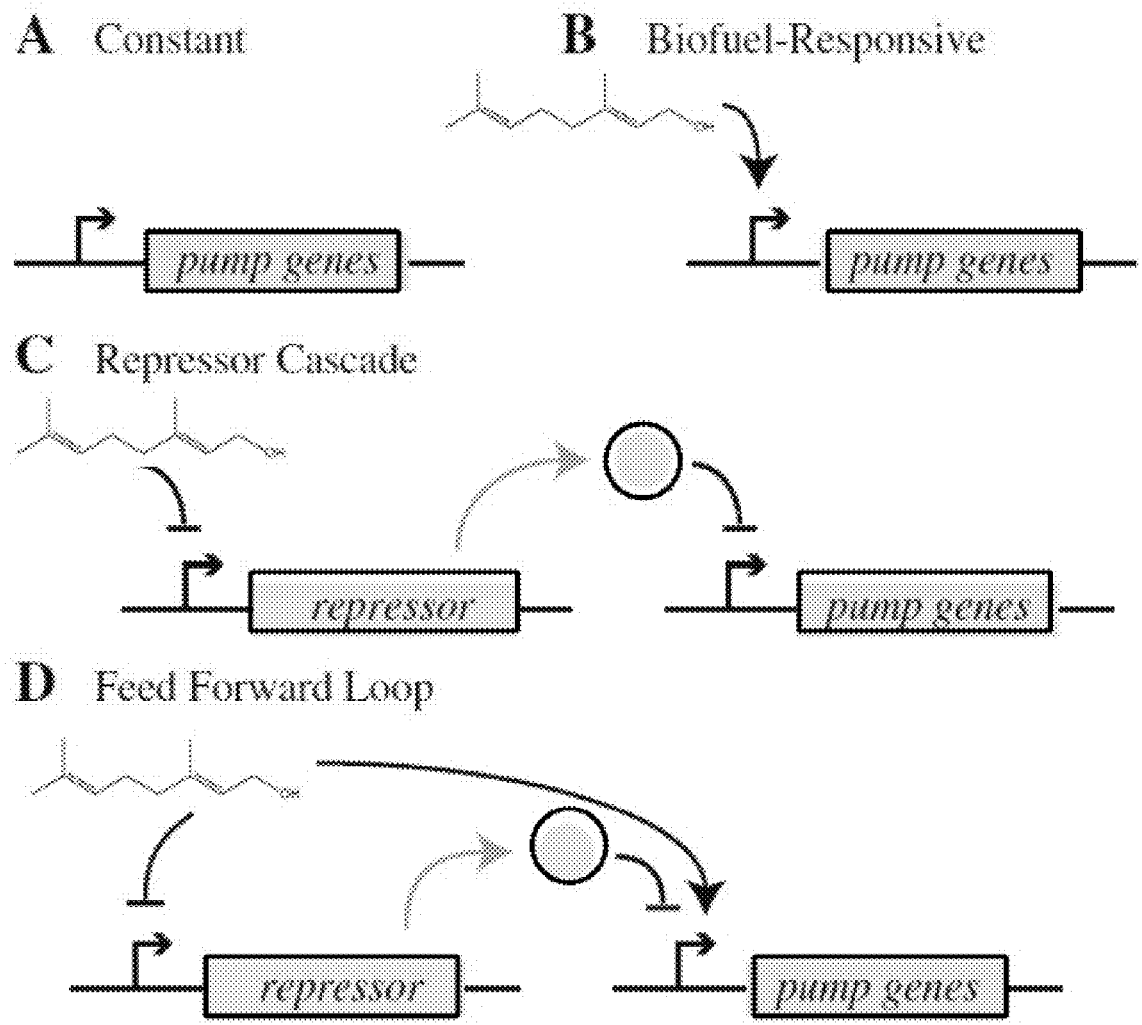

FIG. 8 shows the different schemes for controlling efflux pump expression. (A) With constant control the pump expression is driven by a constitutive promoter. (B) A promoter regulated by a transcription factor that senses biofuel is used to drive efflux pump expression directly. (C) In the repressor cascade biofuel represses production of a transcription factor, which in turn represses efflux pump expression. (D) The feed forward loop uses both biofuel and a transcription factor to control pump expression, while the transcription factor is also controlled by a biofuel-responsive promoter.

DETAILED DESCRIPTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an efflux pump" includes a plurality of such efflux pumps, and so forth.

In this specification and in the claims that follow, reference will be made to a number of terms that shall be defined to have the following meanings:

The terms "expression vector" or "vector" refer to a compound and/or composition that can be introduced into a host cell by any suitable method, including but not limited to transduction, transformation, transfection, infection, electroporation, conjugation, and the like; thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

As used herein, the terms "nucleic acid", "nucleotide" and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA.

The term "operably linked" refers to a functional linkage between a nucleic acid expression control sequence (such as a promoter) and a second nucleic acid sequence, wherein the expression control sequence directs transcription of the nucleic acid corresponding to the second sequence.

When a NCBI/GenBank Accession No. (such as YP_957870) is referred to herein, the accession no. is only that of the gene encoding the inner membrane protein of the operon encoding all of the proteins of the corresponding efflux pump. The entire nucleotide sequence of the operon, and the known/deduced amino acid sequences of the proteins forming the efflux pump, are available from the literature, including the NCBI database (Website for: ncbi.nlm.nih.gov/).

These and other objects, advantages, and features of the invention will become apparent to those persons skilled in the art upon reading the details of the invention as more fully described below.

The Efflux Pump and the Organic Molecule

In some embodiments of the invention, the modified host cell produces the efflux pump. In some embodiments of the invention, the host cell comprises a nucleic acid encoding the efflux pump. The efflux pump is capable of transporting the organic molecule out of the host cell. In some embodiments of the invention, the efflux pump is an efflux pump belonging to the hydrophobe/amphiphile efflux (HAE1) family of resistance-nodulation-division (RND) efflux pumps. In some embodiments of the invention, the efflux pump is one encoded by one or more toluene tolerance genes, or a multidrug efflux pump.

In some embodiments of the invention, the efflux pump is one the following efflux pump encoded by: *Marinobacter aqueolei* operon encoding YP_957870, *Alcanivorax borkumensis* SK2 operon encoding YP_692684, *Pseudomonas putida* KT2440 operon encoding NP_745594, *Pseudomonas aeruginosa* PA01 operon encoding NP_250708, *Pseudomonas aeruginosa* PA01 MexAB-OprM, *Pseudomonas putida* KT2440 MexEF-OprN, *Escherichia coli* K12 operon encoding AcrAB, *Azotobacter vinelandii* AvOP MexEF, *Pseudomonas putida* KT2440 TtgABC, *Pseudomonas aeruginosa* PA01 MexEF-OprN, and *Marinobacter aqueolei* operon encoding YP_960752, and suitable alleles, variants, and mutants thereof. The nucleotide sequence of these operons/genes are available in the literature. The amino acid sequences of the corresponding gene products are available in the literature or can be deduced from the nucleotide sequences described.

The amino acid sequence of a *Marinobacter aqueolei* efflux pump (YP_957870) is as follows (SEQ ID NO:1):

```
  1 minffisrpv fswvlaivam lagimaifvl pvqrypsvap paveiqadyp gasadtvsnt
 61 vvqvieqemt gldnllymgs tadssghatv tltfaagtdp diaqvqvqnk lklaeprlpe
121 vvrqqgisve ksstsflmvm afvstdgrls kldiadfiss elaepigrvt gigsvqvfgs
181 eyamriwldp saltnygltv advsaaieaq naqvtagqlg glpavegqql natvtaqtll
241 tsteefrnil lksmpdgsrv rlgdvarvel gggavqidtf ydgepaaglg inlapgansl
301 avteavkarl qelepyfpeg veirypyqta pfveasidav vttiieaial vvlvmlvflq
361 swratlipai aipvvllgtf aimaafgfsi nmltlfglvl aigllvddai vvvenvervm
421 hedglspmea trksmgqias aligigvvls avfipmaffp gstgaiyrqf slsiagamvl
481 svlvalilsp mlcgrilkpt hertllqklf gwfeaglgrl trgyvrlvgh tarhawlytl
541 aflgivglva vlfvrlpggf lpaedqgfav vqyqlpagat qqrtidtiqv iedyfmdqde
601 vqglftiagf sfagraqnag lafvnlkpws erdpetqsad aiiqranral aglvrdgraf
661 afnlppipel gqalgfelrl qdrgaighea lmaaggqllq laaespvlts vrpngladnp
721 rykvdidyek aqalgiepse isrllsvtwg sqyvndflhe grvkrvyvqg dapfrmlped
781 feawylraan gemtplsevt ngrweygspr lerfngvpsr qiqgepapgy stgeamaeve
```

-continued

```
841 rliaqlpdgv agawsglsyq erqagaqasl lyalsalvvf lalaalyesw tipisvmlav 901 plgvlgavla amvrglpndv ffqvgilttv gvtarnaill vefarsledq gmklieatke 961 aarvrlrpil mtsvafgmgv lplafasgag attriaigta vlggmisati latffiplfy 1021 vvvrritdfl sgsrdqddsa aaapgrangg vaddr
```

The amino acid sequence of an *Alcanivorax borkumensis* SK2 efflux pump (YP_692684) is as follows (SEQ ID NO:2):

```
  1 marffidrpi fawviaiimm magalaiytl pieqyptvap pqvsiagnyp gasaktveds 61 vtqvieqqmn gidnllymss ssdsfgnaav nitfapgtdp diaqvqvqnk lqlatpllpq 121 evqqqgmqvt kssdsflmva gftsedgsls radladyvas nvqdpvsrvp gvgqiqlfgs 181 pyamrvwldp nklnkfdltp qdvtqtievq nnqvasgqlg gapavegqql natiiaqtrl 241 edvdqfenil lkvnpdgsrv flkdvarvel aaqnydvqgr yngqpaagla islatganal 301 dtaealrarl aelqpyfpdk memvfpydtt pfvsisieev vhtlfeaiil vflvmylflq 361 nfratliptl avpvvllgtf avlaafgfsi ntltmfgmvl aigllvddai vvvenvervm 421 heeglppkea trksmgqitg alvgialvls avfvpmaffp gstgaiyrqf sitivsamvl 481 svlvaliltp alcatmlkak dsehqtdhgf fgwfnrtfdk ssrryqgsve kilgrrgryl 541 fiyvvivgvl gfsfmrlpss flpeedqgil ftlvtlpags tqeqtvkvle kmedyylnee 601 asavdglftv agfsftgrgq nagmafvnlk dwserdlsvd gadnvvaram gyfstiream 661 mfalnppsip elgnasgfdf qlldqsgqgh ealiqarnqm lgmaaqdprl agvrpngled 721 spqyqididq qkakalglsi sdinstlqia wgssyvnnfv drgrvkrvyv qadapyrmlp 781 envndwfvrn nqgkmvpfst fatghwtygs pkleryngvs svniqgnaap gystgdamda 841 meelsaklpa gfgfewtgms yqerqsgdqa palyvisllv vflclaalye swsipfavml 901 vvplgilgav laatfrdlnn dvffqvgllt tiglsaknai liaefalele qkgehllkat 961 leavrmrlrp ilmtslafml gvtplmistg agagarnaig tgvfggmlta tvlaiffipl 1021 fyvavrklsg vpldgkkkgk e
```

The amino acid sequence of a *Pseudomonas putida* KT2440 efflux pump (NP_745594) is as follows (SEQ ID NO:3):

```
  1 mpqffidrpv fawvvalfil lagalaipql pvaqypnvap pqveiyavyp gasaatmdes 61 vvslieqeln gadnllyfes qsslgsatit atfapgthpd laqvdvqnrl kvvesrlprp 121 vtqqglqvek vstgflllat ltsedgklde talsdilarn vmdeirrlkg vgkaqlygse 181 ramriwidpr kligfnltpn dvaeaiaaqn aqvapgsigd lpsrstqeit anvvvkgqls 241 spdefaaivl ranpdgstvt igdvarveig aqeyqygtrl ngkpatafsv qlspganame 301 tatlvrakmq dlaryfpegv kydipydtsp fvkvsieqvi ntlfeamllv favmflflqn 361 lrytliptlv vpvalmgtfa vmlamgfsvn vltlfgmvla igilvddaiv vvenverima 421 eeglppkqat rkamgqisga ivgitlvlva vflpmafmqg svgviyqqfs lsmavsilfs 481 aflalsltpa lcatllkpva kgehherkgf fgwfnrrfes msngyqrwvv qalkrsgryl 541 lvyavllavl gygfsqlpta flptedqgyt itdiqlppga srmrteqvaa qieahnaeep 601 gvgnttlilg fsfsgsgqna alafttlkdw sergaddsaq siadratmaf tqlkdaiays 661 vlpppidglg estgfefrlq drggmghael maardqlles askskvltnv reaslaespq
```

-continued

```
 721 vqleidrrqa nalgvsfadi gtvldvavgs syvndfpnqg rmqrvvvqae gdqrsqvedl 781 lnihvrndsg kmvplgafvq arwvsgpvql tryngypavs isgepaagys sgeamaever 841 lvaqlpagtg lewtglslqe rlsgsqapll malsllvvfl claalyesws iptavllvvp 901 lgvlgavlav tlrgmpndvf fkvglitlig lsaknailii efakhlvdqg vdaadaavqa 961 arlrlrpivm tslafilgvv plaiasgass asqqaigtgv iggmlsatla vvfvpvffvv 1021 vmrlsgrrqa hdsdgqpvpr es
```

The amino acid sequence of a *Pseudomonas aeruginosa* PA01 efflux pump (NP_250708) is as follows (SEQ ID NO:4):

```
   1 marffidrpv fawvislliv lagvlairfl pvaqypdiap pvvnvsasyp gasakvveea 61 vtaiieremn gapgllytka tsstgqaslt ltfrqgvnad laavevqnrl kivesrlpes 121 vrrdgiyvek aadsiqlivt ltsssgryda melgeiassn vlqalrrveg vgkvetwgae 181 yamriwpdpa kltsmnlsas dlvnavrrhn arltvgdign lgvpdsapis atvkvddtlv 241 tpeqfgeipl riradggair lrdvarvefg qseygfvsrv nqmtatglav kmapgsnava 301 takriratld elsryfpegv synipydtsa fveisirkvv stlleamllv favmylfmqn 361 fratliptlv vpvallgtft vmlglgfsin vltmfgmvla igilvddaii vvenverlma 421 eeglsphdat vkamrqisga ivgitvvlvs vfvpmaffsg avgniyrqfa vtlavsigfs 481 aflalsltpa lcatllrpid adhhekrgff gwfnraflrl tgryrnavag ilarpirwml 541 vytlvigvva llfvrlpqaf lpeedqgdfm imvmqpegtp maetmanvgd verylaehep 601 vayayavggf slygdgtssa mifatlkdws erreasqhvg aiverinqrf aglpnrtvya 661 mnspplpdlg stsgfdfrlq drggvgyeal vkardqllar aaedprlanv mfagqgeapq 721 irldidrrka etlgvsmdei nttlavmfgs dyigdfmhgs qvrkvvvqad gakrlgiddi 781 grlhvrneqg emvplatfak aawtlgppql tryngypsfn legqaapgys sgeamqameq 841 lmqglpegia hewsgqsfee rlsgaqapal falsvlivfl alaalyesws iplavilvvp 901 lgvlgallgv slrglpndiy fkvglitiig lsaknailii evakdhyqeg msllqatlea 961 arlrlrpivm tslafgfgvv plalssgags gaqvaigtgv lggivtatvl avflvplffl 1021 vvgrlfrlrk aprtgnspqi pteqa
```

45

The amino acid sequence of a *Marinobacter aqueolei* efflux pump (YP_960752) is as follows (SEQ ID NO:5):

```
   1 mprffierpi fawvvalmlm lggglavknl avnqfpdvap paialsvnyp gasaqtvqdt 61 vvqvieqqln gldglryiss esnsdgsmti iatfeqgtdp diaqvqvqnk lqlanpllpe 121 evqrqgirvs kykvnfftvf altspdgkyt qgdladyivs niqdpvartq gvgdfllfgs 181 qyamrlwldp eklnsyqltp qdvinsvraq nvqvsagqlg glptaegvql qatvigkqrm 241 ktaeefenil lkvnpdgsqv rladvaevnl gnenyattgk yngapaagma lrlatganql 301 etagrvketl aelerflpeg veivfpydtt pvvsasietv amtlieavvl vflvmflflq 361 swratiiptl avpvvllatf gvlyafgftv nvmtmfamvl aigllvddai vvvenverlm 421 eeeglspkea akksmdqisg allgiglvis avflpmaffg gstgviyrqf svtiisamsf 481 svlvafiftp alcatllkpg dqhvrkgffg wfnrtfdrsa dryksgvsyl ikrkgrfmgv 541 ylllvvavgf lfkglptafl pdedqgvmiv mvqlptnatg erteavlaea gnylleeese 601 vvksvmsvrg fnfagrgqns gilfvdlkpf adresfaqsv falagrsgar faqikdaivf
```

```
 661 pivppailel gnatgfdlyl kdngaighha lmaatnefis ranaapelnm vrhnglpdep 721 qyqviiddek arllqvsiad inatmsaawg ssyvndflhn grvkkvyvqg kpdsrlaped 781 fdkwfvrnaq gemvpfaafa tgewvfgspr lqryqglpat qiqgapangy stgdamaale 841 riaadlpqgl gleytglsfe ekqagnqamm lyllsilvvf lclaalyesw sipfavimlv 901 plgvlgavla tmarglsndv ffqvgmlttm glaaknaili vefarqlyeq egkpllqata 961 eaarlrlrpi imtslafifg vlpmaiasga ssasqhaigt avvggtlaat ilaiffvplf 1021 yvfvvgltgk rksadd
```

The suitable alleles, variants, or mutants of the efflux pumps include the alleles, variants, and mutants of any of the efflux pumps described herein that comprise an amino acid sequence having at least 70% identity as compared to the amino acid sequence of the wild-type efflux pump, and is able to export an organic molecule from a cell using the proton motive force. In some embodiments of the invention, the allele, variant, or mutant of an efflux pump comprises an amino acid sequence having at least 80% identity as compared to the amino acid sequence of the wild-type efflux pump. In some embodiments of the invention, the allele, variant, or mutant of an efflux pump comprises an amino acid sequence having at least 90% identity as compared to the amino acid sequence of the wild-type efflux pump. In some embodiments of the invention, the allele, variant, or mutant of an efflux pump comprises an amino acid sequence having at least 95% identity as compared to the amino acid sequence of the wild-type efflux pump. In some embodiments of the invention, the allele, variant, or mutant of an efflux pump comprises an amino acid sequence having at least 99% identity as compared to the amino acid sequence of the wild-type efflux pump.

In some embodiments of the invention, the organic molecule is geranyl acetate, and the efflux pump is encoded by *Marinobacter aqueolei* operon encoding YP_957870, *Alcanivorax borkumensis* SK2 operon encoding YP_692684, *Pseudomonas putida* KT2440 operon encoding NP_745594, *Pseudomonas aeruginosa* PA01 operon encoding NP 250708, *Pseudomonas aeruginosa* PA01 MexAB-OprM, *Pseudomonas putida* KT2440 MexEF-OprN, *Pseudomonas putida* KT2440 TtgABC, or *Escherichia coli* K12 AcrAB.

In some embodiments of the invention, the organic molecule is α-pinene or farnesyl hexanoate, and the efflux pump is encoded by *Azotobacter vinelandii* AvOP MexEF, *Pseudomonas putida* KT2440 TtgABC, *Pseudomonas putida* KT2440 operon encoding NP_745594, *Pseudomonas putida* KT2440 MexEF-OprN, *Pseudomonas aeruginosa* PA01 MexAB-OprM, *Pseudomonas aeruginosa* PA01 encoding NP_250708, *Pseudomonas aeruginosa* PA01 MexEF-OprN, *Marinobacter aqueolei* operon encoding YP_960752, *Marinobacter aqueolei* operon encoding YP_957870, *Alcanivorax borkumensis* SK2 operon encoding YP_692684, or *Escherichia coli* K12 operon encoding AcrAB.

In some embodiments of the invention, the organic molecule is geraniol, and the efflux pump is encoded by *Escherichia coli* K12 operon encoding AcrAB In some embodiments of the invention, the organic molecule is limonene, and the efflux pump is encoded by *Pseudomonas putida* KT2440 MexEF-OprN, *Pseudomonas aeruginosa* PA01 MexAB-OprM, *Marinobacter aqueolei* operon encoding YP_957870, *Alcanivorax borkumensis* SK2 operon encoding YP_692684, or *Escherichia coli* K12 operon encoding AcrAB.

In some embodiments of the invention, the organic molecule is toxic to the host cell. In some embodiments of the invention, the organic molecule is a biofuel, bio-gasoline, bio-diesel, bio-jet fuel, or precursors or candidates thereof. In some embodiments of the invention, the organic molecule is geranyl acetate, geraniol, α-pinene, limoene, or faresyl hexanoate.

The Host Cell and the Nucleic Acid

The present invention provides for a modified host cell comprising a first nucleic acid encoding the efflux pump, and a second nucleic acid encoding one or more enzymes for producing the organic molecule, wherein the modified host cell is capable of expressing the efflux pump and the one or more enzymes for producing the organic molecule. In some embodiments of the present invention, the first nucleic acid and the second nucleic acid are each independently on a vector or integrated into a chromosome. The vector can be an expression vector or a plasmid. In some embodiments of the present invention, the first nucleic acid and the second nucleic acid are on the same vector, such as an expression vector or a plasmid. In some embodiments of the present invention, the vector is capable of stable maintenance in a host cell.

The nucleic acid used in the present invention can be a recombinant nucleic acid. The recombinant nucleic acid can be a double-stranded or single-stranded DNA. The recombinant nucleic acid can also comprise promoter sequences for transcribing the efflux pump or one or more enzymes for producing the organic molecule in the host cell. The recombinant nucleic acid can also comprise sequences sufficient for having the recombinant nucleic acid stably replicate in the host cell. The recombinant nucleic acid can be a replicon capable of stable maintenance in the host cell. In some embodiments, the replicon is a vector or expression vector, or a plasmid.

In some embodiments of the invention, the gene(s) encoding the efflux pump is operatively linked to a promoter that produces constitutive expression or is modulated, such as modulated by the amount or concentration of the organic molecule or a precursor of the organic molecule in the host cell. The gene(s) of the efflux pump can be operatively linked to promoters and control elements that modulate the expression of the efflux pump a manner described in FIG. 8. Each modulation scheme is described in Dunlop et al. ("A model for improving microbial biofuel production using a synthetic feedback loop", *Syst. Synth. Biol.*, published online Feb. 25, 2010; which is incorporated by reference).

In some embodiments of the invention, the host cell is a Gram-negative bacterium. In some embodiments of the invention, the host cell is a proteobacteria bacterium. In some embodiments of the invention, the bacterium is any bacterium that produces the organic molecule. In some embodiments of the invention, the bacterium is an enteric bacterium. In some embodiments of the invention, the bacterium is of the genus *Planctomyces, Bradyrhizobium, Rhodobacter, Rhizobium, Myxococcus, Klebsiella, Azotobacter, Escherichia, Salmonella, Pseudomonas, Caulobacter, Chlamydia, Acinetobacter, Sinorhizobium, Vibrio,* or *Zymomonas*. In some embodiments of the invention, the efflux pump is native to the host cell. In some embodiments of the invention, the efflux pump is heterologous to the host cell. In some embodiments of the invention, the bacterium is *E. coli.*

In some embodiments of the invention, the modified host cell produces the organic molecule. In some embodiments of the invention, the host cell comprises a nucleic acid encoding one or more enzymes for producing the organic molecule. In some embodiments of the invention, the host cell in its wild-type form does not produce the organic molecule.

The modified host cells of the present invention are useful in that they have one or more of the following advantages: (1) the host cells are capable of producing large amounts of the organic molecules, and (2) the host cells are capable of growing in an environment that has a high concentration of the organic molecule.

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in the host cells and those that remain episomal or those that integrate into the host cell genome.

The vectors may be chosen to contain control sequences operably linked to the resulting coding sequences in a manner that expression of the coding sequences may be effected in an appropriate host cell. Suitable control sequences include those that function in the host cells. If the cloning vectors employed to obtain encoded peptides of interest lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for single cell cultures of various types of organisms are well known in the art. Control elements include promoters, optionally containing operator sequences, and other elements depending on the nature of the host, such as ribosome binding sites. Particularly useful promoters for host cells include those promoters that are native to the peptide of interest. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433; hereby incorporated by reference), can be used.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The nucleic acid sequences or nucleotide sequences described herein, or a mixture of such sequences, can be cloned into one or more recombinant vectors as individual cassettes, with separate control elements or under the control of a single promoter. Methods for introducing the nucleic acid into suitable host cells are known to those of skill in the art and typically include the use of $CaCl_2$ or other agents, such as divalent cations, lipofection, DMSO, protoplast transformation, conjugation, and electroporation.

REFERENCES CITED

1. Peralta-Yahya, P. P. and J. D. Keasling, *Advanced biofuel production in microbes*. Biotechnology Journal. 5(2): p. 147-162.
2. Ramos, J. L., et al., *Mechanisms of solvent tolerance in gram-negative bacteria*. Annu Rev Microbial, 2002. 56: p. 743-768.
3. Fortman, J. L., et al., *Biofuel alternatives to ethanol: pumping the microbial well*. Trends in Biotechnology, 2008. 26(7): p. 375-381.
4. Lee, S. K., et al., *Metabolic engineering of microorganisms for biofuels production: from bugs to synthetic biology to fuels*. Current Opinion In Biotechnology, 2008. 19(6): p. 556-563.
5. Stephanopoulos, G., *Challenges in engineering microbes for biofuels production*. Science, 2007. 315(5813): p. 801-804.
6. Dunlop, M. J., J. D. Keasling, and A. Mukhopadhyay, *A model for improving microbial biofuel production using a synthetic feedback loop*. Systems & Synthetic Biology, 2010.
7. Harvey, B. G., M. E. Wright, and R. L. Quintana, *High-Density Renewable Fuels Based on the Selective Dimerization of Pinenes*. Energy & Fuels. 24: p. 267-273.
8. Paulsen, I. T., M. H. Brown, and R. A. Skurray, *Proton-dependent multidrug efflux systems*. Microbiological Reviews, 1996. 60(4).
9. Bavro, V. N., et al., *Assembly and channel opening in a bacterial drug efflux machine*. Molecular Cell, 2008. 30(1): p. 114-121.
10. Putman, M., H. W. van Veen, and W. N. Konings, *Molecular properties of bacterial multidrug transporters*. Microbiology And Molecular Biology Reviews, 2000. 64(4): p. 672-693.
11. Ramos, J. L., et al., *Efflux pumps involved in toluene tolerance in Pseudomonas putida DOT-T1E*. Journal Of Bacteriology, 1998. 180(13): p. 3323-3329.

12. Rojas, A., et al., *Three efflux pumps are required to provide efficient tolerance to toluene in Pseudomonas putida DOT-T1E.* Journal Of Bacteriology, 2001. 183 (13): p. 3967-3973.
13. Kieboom, J., et. al., *Identification and molecular characterization of an efflux pump involved in Pseudomonas putida S12 solvent tolerance.* Journal Of Biological Chemistry, 1998. 273(1): p. 85-91.
14. Kieboom, J., et al., *Active efflux of organic solvents by Pseudomonas putida S12 is induced by solvents.* Journal Of Bacteriology, 1998. 180(24): p. 6769-6772.
15. Isken, S, and J. A. M. De Bont, *The solvent efflux system of Pseudomonas putida S12 is not involved in antibiotic resistance.* Applied Microbiology And Biotechnology, 2000. 54(5): p. 711-714.
16. Li, X. Z., L. Zhang, and K. Poole, *Role of the multidrug efflux systems of Pseudomonas aeruginosa in organic solvent tolerance.* Journal Of Bacteriology, 1998. 180 (11): p. 2987-2991.
17. Nikaido, H. and Y. Takatsuka, *Mechanisms of RND multidrug efflux pumps.* Biochimica Et Biophysica Acta-Proteins And Proteomics, 2009. 1794(5): p. 769-781.
18. Tseng, T.-T., et. al., *The RND Permease: Superfamily: An Acient, Ubiquitous and Diverse Family that Includes Human Disease and Development Proteins.* J. Mol. Microbiol. Biotechnolo., 1999. 1: p. 107-125.
19. Strogatz, S. H., *Nonlinear Dynamics and Chaos.* 1994: Westview Press.
20. Hardin, G., *Competitive Exclusion Principle.* Science, 1960. 131(3409): p. 1292-1297.
21. Levin, S. A., *Community Equilibria And Stability, And An Extension Of Competitive Exclusion Principle.* American Naturalist, 1970. 104(939): p. 413-423.
22. Rutherford, B. J., et al., *Functional Genomic Study of Exogenous n-Butanol Stress in Escherichia coli.* Applied And Environmental Microbiology. 76(6): p. 1935-1945.
23. Bokma, E., et al., *Directed evolution of a bacterial efflux pump: Adaptation of the E-coli TolC exit duct to the Pseudomonas MexAB translocase.* Febs Letters, 2006. 580(22): p. 5339-5343.
24. Atsumi, S., T. Hanai, and J. C. Liao, *Non fermentative pathways for synthesis of branched-chain higher alcohols as biofuels.* Nature, 2008. 451(7174): p. 86-U13.
25. Steen, E. J., et al., *Metabolic engineering of Saccharomyces cerevisiae for the production of n-butanol.* Microbial Cell Factories, 2008. 7: p.
26. Lee, A., et al., *Interplay between efflux pumps may provide either additive or multiplicative effects on drug resistance.* Journal Of Bacteriology, 2000. 182(11): p. 3142-3150.
27. Dehal, P. S., et al., *MicrobesOnline: an integrated portal for comparative and functional genomics.* Nucleic Acids Research. 38: p. D396-D400.
28. Krogh, A., et al., *Predicting transmembrane protein topology with a hidden Markov model: Application to complete genomes.* Journal Of Molecular Biology, 2001. 305(3): p. 567-580.
29. Altschul, S. F., et al., *Gapped BLAST and PSI-BLAST: a new generation of protein database search programs.* Nucleic Acids Research, 1997. 25(17): p. 3389-3402.

The invention having been described, the following examples are offered to illustrate the subject invention by way of illustration, not by way of limitation.

Example 1

Efflux Pumps can Improve E. coli Biofuel Tolerance

Many of the compounds being considered as candidates for next generation biofuels are toxic to microorganisms [1]. This introduces an undesirable trade-off when engineering metabolic pathways for biofuel production because strains must balance production against survival. Cellular export systems, such as efflux pumps, provide a direct mechanism for reducing biofuel toxicity [2]. To identify novel biofuel pumps, we constructed a library of heterologously expressed efflux pumps in *E. coli* and tested it against a representative set of biofuel candidates. In order to efficiently screen for improved tolerance, we devised a competitive growth assay and used it to identify pumps that improved survival. A model of the assay suggests that competitive exclusion will result in a dramatic overrepresentation of strains containing beneficial efflux pumps in the population. We test these predictions experimentally, finding that in the presence of a stressor, beneficial efflux pumps quickly distinguish themselves. In this work we have identified several efflux pumps, some previously uncharacterized, that restore growth in the presence of biofuel. Our findings may be applied to future production strains to improve yield while maintaining cell viability.

We focus on a family of efflux pumps that has previously been shown to export biofuel-like compounds. We examine the efficacy of a library of efflux pumps against a range of compounds that are candidate biofuels or biofuel precursors.

Figure 4:
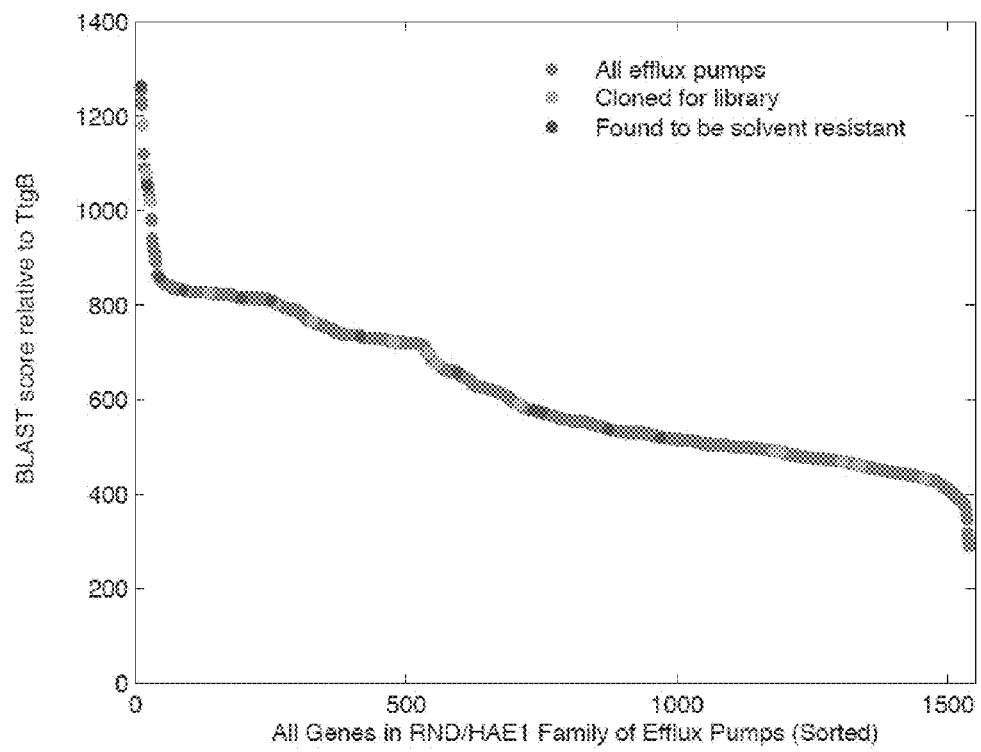
FIG. 4 shows the homology of all annotated HAE1 efflux pumps to TtgB (blue). Efflux pumps included in the library (orange and red), and those library members that showed resistance to at least one solvent (red). Homology search is limited to the two large periplasmic loops (Methods).

Using *E. coli* as our engineering host, we asked whether expression of heterologous efflux pumps could reduce the toxicity of biofuels. We constructed a library of efflux pumps by searching for pumps classified as HAE1 from all sequenced gram-negative bacterial genomes (Methods). From this list, we selected representative candidates that spanned a broad range of sequence space, including those that were both very similar and very dissimilar to a known solvent resistant pump (FIG. 4). To construct the library, efflux pump genes were amplified from the genomic DNA of the selected bacterium, cloned into a vector backbone, and transformed into *E. coli* DH1 ΔacrAB (Methods). In total, our library contains 43 efflux pump operons, most of which have not been previously characterized for biofuel tolerance.

Figure 1:
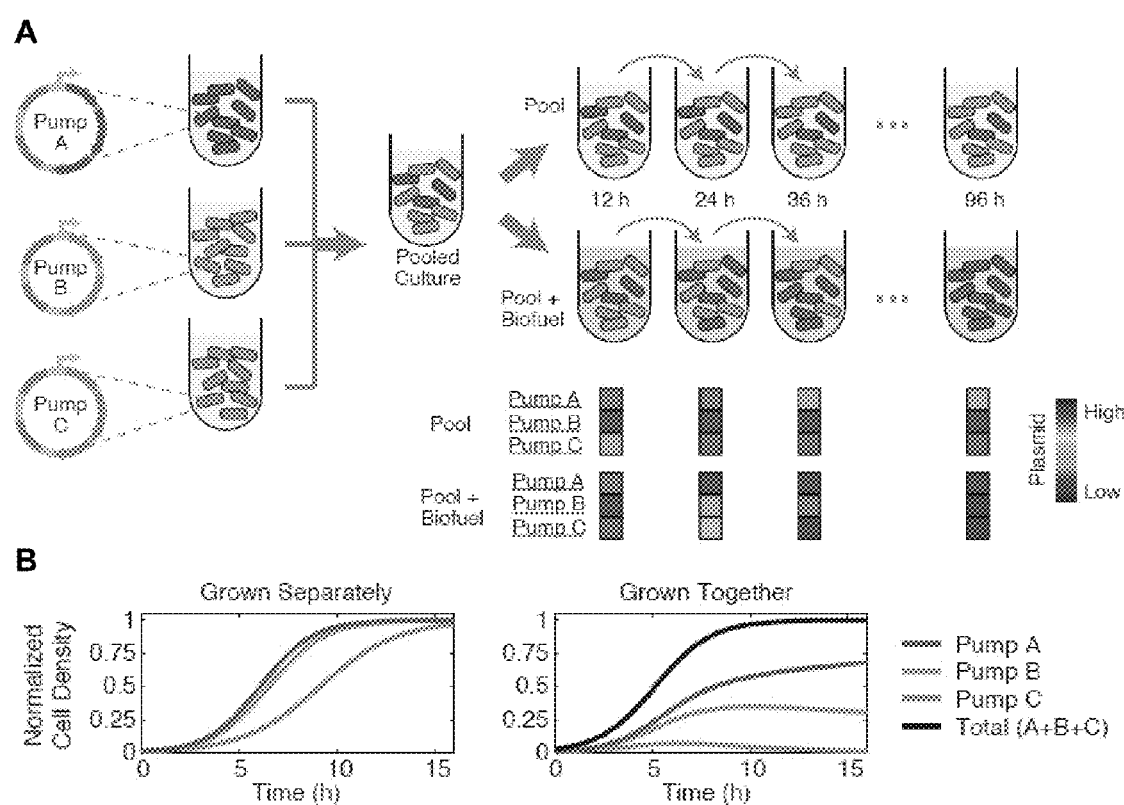
FIG. 1 shows that the competition assay screens for efflux pumps that provide biofuel resistance. (A) Plasmids containing the operons for individual efflux pumps are transformed into cells. These strains are grown independently and then pooled in equal proportion. The pooled culture is grown both with and without biofuel for 96 hours, diluting into fresh medium every 10-14 hours. At selected time points cultures are saved, plasmids isolated, and the relative levels of each efflux pump plasmid are quantified. If certain plasmids provide a growth advantage, they will become overrepresented in the culture. (B) Simulations of competitive exclusion. Grown separately, the growth curve of a strain is dependent only on its growth rate. When grown together, as in the competition assay, strains with higher growth rates will dominate the population. Simulation parameters are $d_A=0.75$, $d_B=0.7$, $d_C=0.5$, and $K=1$.

In order to screen the efflux pump library against a variety of biofuels we devised a competition-based strategy to select for pumps that improved biofuel tolerance (FIG. 1A). Cells containing plasmids with individual pumps were grown separately and then pooled so that all individual strains were represented equally. This pooled culture was then grown both with and without biofuel, and maintained through serial dilutions every 10-14 hours over a total of 96 hours. At each dilution time point, plasmids from each culture were isolated and a custom microarray was used to quantify the amount of each efflux pump plasmid present in the culture (Methods).

Figure 5:
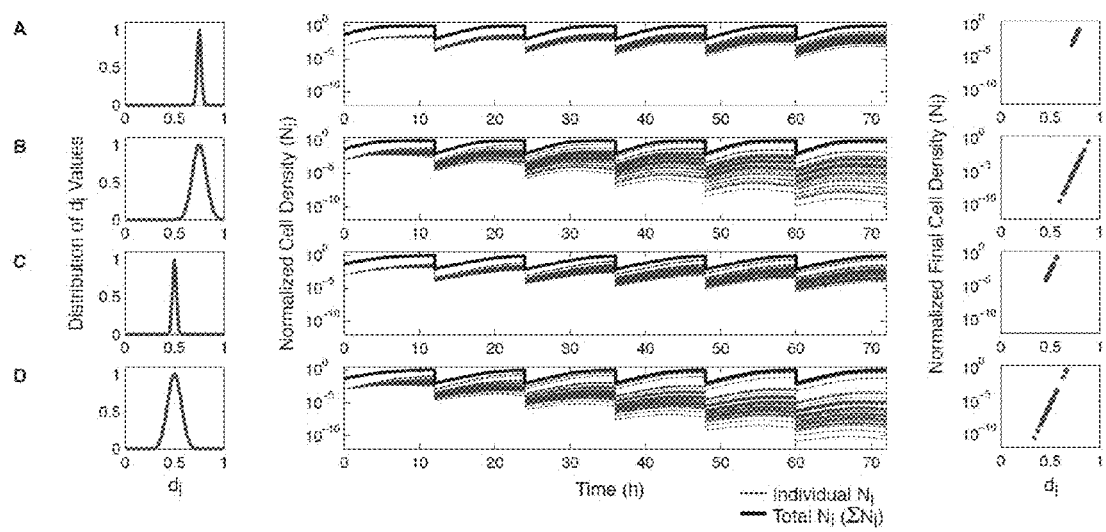
FIG. 5 shows simulations of competitive growth for several growth rate distributions. The total number of competitors is 43. The mean and standard deviation of the underlying distribution that $d_i$ is drawn from are (A) $\mu_d=0.75$, $\sigma_d=0.02$; (B) $\mu_d=0.75$, $\sigma_d=0.07$; (C) $\mu_d=0.5$, $\sigma_d=0.02$; (D) $\mu_d=0.5$, $\sigma_d=0.07$. The second column of plots shows typical time course simulation data where the 1:100 serial dilution is modeled by dividing all cell densities by 100 every 12 hours. Note that final $N_i$ distributions look similar for $d_i$ distributions that have similar standard deviations. Thus, it is challenging to distinguish between experiments where all pumps perform well and those where all pumps perform poorly (c.f. pool and n-butanol in FIG. 3A).

A mathematical model of competitive growth suggests that strains containing efflux pumps that reduce biofuel toxicity will rapidly dominate the culture by competitive exclusion [19-21]. The model predicts that when strains with a range of growth rates are grown separately, those with similar growth rates will have similar growth curves (FIG. 1B). However, when the same strains are grown together in a co-culture, those with higher growth rates will quickly outperform those with lower growth rates. Thus, we expect that those strains expressing efflux pumps that help to mitigate biofuel toxicity will have a growth advantage, and will quickly dominate the co-cultures. Simulations of the competition assay show that, in cases where specific pumps provide a growth rate advantage, the co-culture will be primarily composed of strains with the highest efficacy pumps after a small number of growth cycles (FIG. 5).

Figure 2:
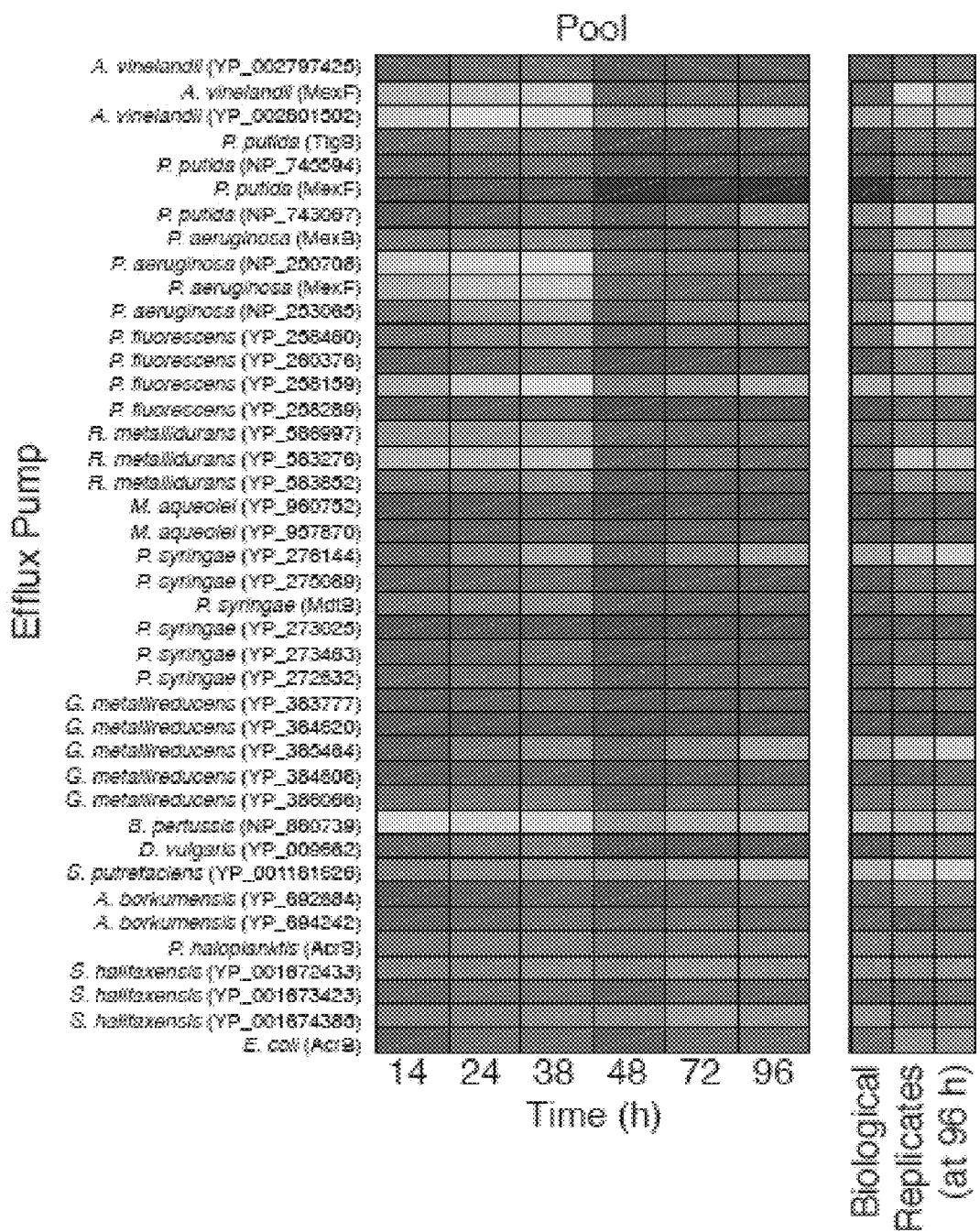
FIG. 2 shows the competitive growth time course with and without biofuel. (A) Pooled culture containing all strains shows performance of all pumps to be similar in the absence of an inhibitor. Each row represents the quantity of a different efflux pump-containing plasmid; columns show time points in the serial dilution competition experiment. Biological replicate data from the 96 hour time point show similar results for the three replicates. For each efflux pump the host and GenBank accession number (or protein name, if annotated) of the inner membrane protein are given, further information is provided in Table 1. (B) When the pooled culture was grown in the presence of 2% geranyl acetate some efflux pumps improve cell survival. Positive and negative hybridization controls label all efflux pump plasmids and a pump-free plasmid (Methods). All data are shown in log scale with arbitrary units (A.U.).
Figure 2:
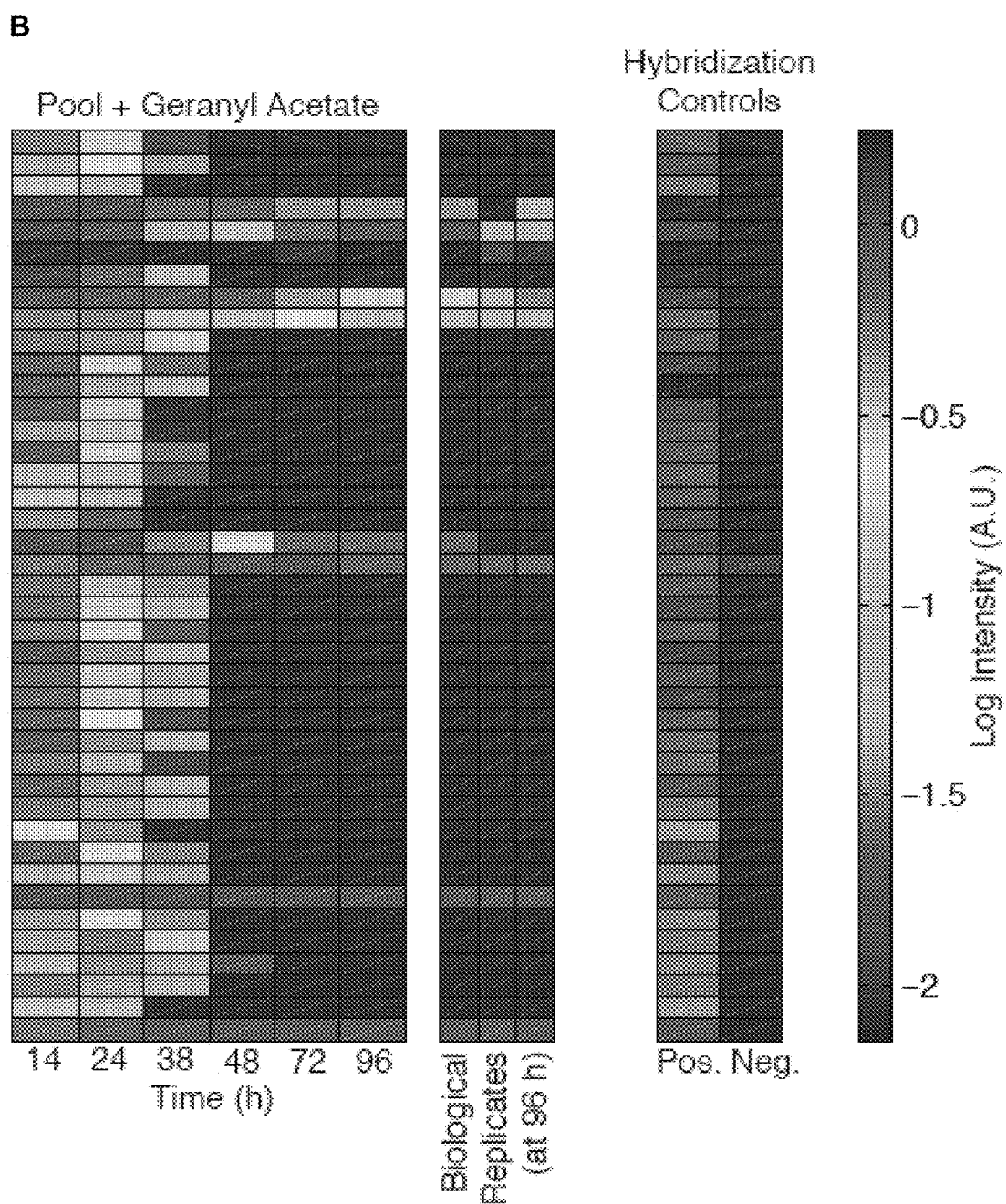

To test our predictions experimentally we first asked how the composition of the competition cultures changes over time. When the pooled culture is grown on its own without any biofuel, the efflux pumps are all represented equally, indicating that no strain has a particular advantage (FIG. 2A). This remains true over the course of the 96 hour experiment, showing that under these induction conditions, any burden of pump expression is roughly equivalent for all strains.

In contrast, when the pooled culture was grown in the presence of the bio-diesel candidate geranyl acetate, some efflux pumps conferred a distinct advantage (FIG. 2B). Although all strains start out with equal representation, after 38 hours the population composition changes, with cells containing the advantageous efflux pumps becoming an increasingly larger proportion of the population. Biological replicates show that this set of competition winners is obtained regardless of other factors that affect experimental variability.

The efflux pumps that enhance tolerance to geranyl acetate come from a variety of organisms and include both known and previously uncharacterized pumps. In particular, two marine bacteria that were isolated in hydrocarbon-rich seawater, *Marinobacter aqueolei* and *Alcanivorax borkumensis*, each contribute efflux pumps that increase survival (YP_957870 and YP_692684). Several pumps from *Pseudomonas putida* KT2440 and *Pseudomonas aeruginosa* PA01 also survived the competition, including two putative pumps (NP_745594 and NP_250708) and the solvent resistant MexB, MexF, and TtgB pumps. The plasmid-based copy of the *E. coli* efflux pump AcrB also survived the competition.

Figure 3:
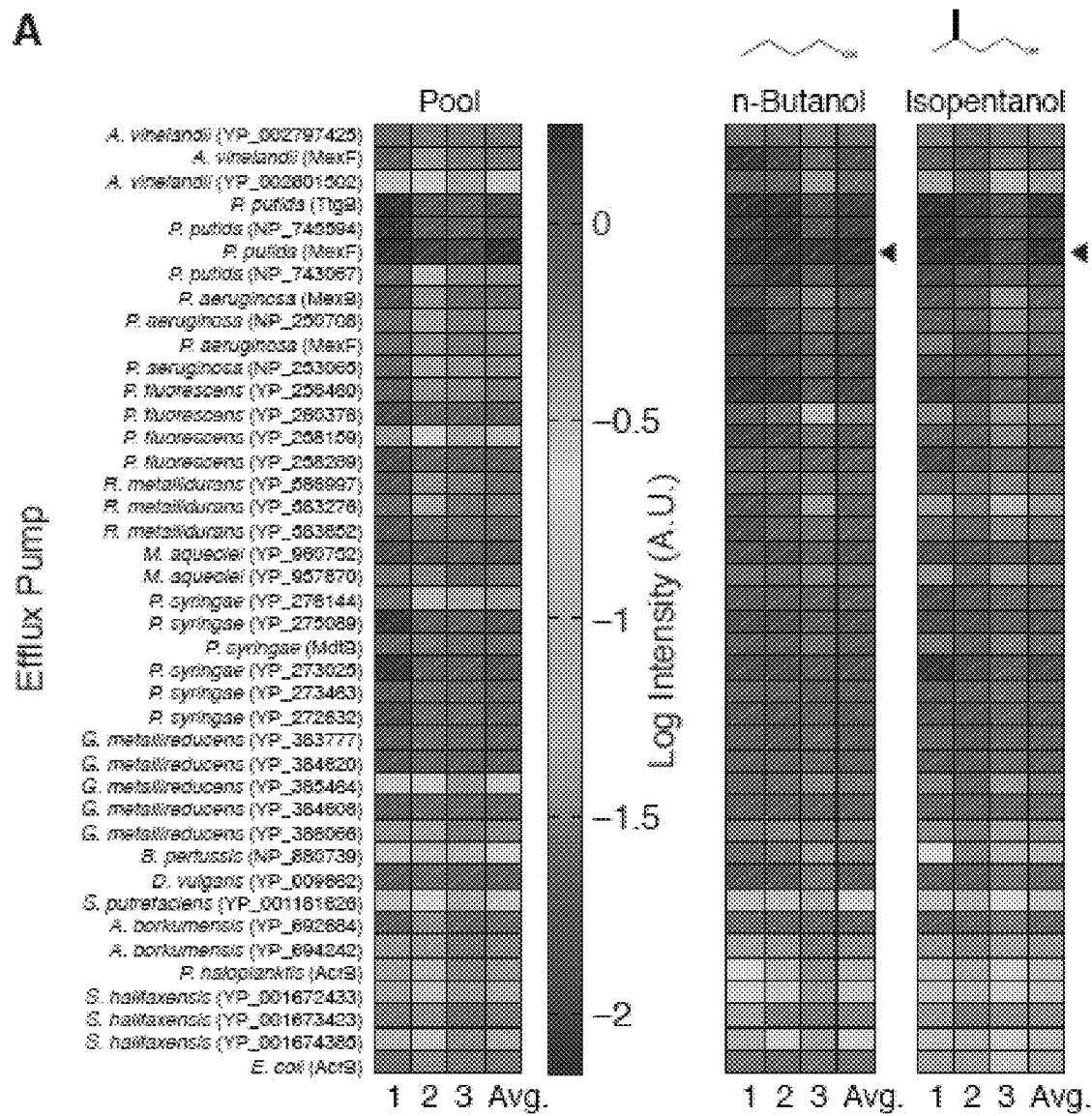
FIG. 3 shows efflux pumps can improve tolerance to selected biofuels. (A) Plasmid levels for each of the efflux pumps in the library after 72 hours of a serial dilution competition experiment. The pool data shows results from cultures grown without an inhibitor. For all others, biofuel was added at an inhibitory level (Methods). Figure shows three biological replicates and their average. All efflux pumps perform similarly in the presence of n-butanol and isopentanol. (B) Inhibition studies comparing the top performing pump (shown with an arrow in (A)) and a negative control show that the pump provides no growth advantage. The biofuel concentration that was used in the competition experiment is shown with a gray dashed line. Taken together, (A) and (B) demonstrate that none of the efflux pumps we tested can improve tolerance to n-butanol or isopentanol. (C) Competition results for biofuels where efflux pumps provide a growth advantage. (D) Top performing pumps show improvements over the negative control strain. Measurements shown in (B) and (D) were taken in triplicate and averaged; error bars show standard deviation. (E) Targeted studies on α-pinene show that the competition experiment has correctly sorted pumps based on performance. Five representative pumps, marked with * in (C), are growth with and without α-pinene. In the absence of α-pinene all efflux pump cultures grow similarly, though not quite as well as the pump-free negative control. With 2% α-pinene, growth differences become apparent and higher ranked pumps show better survival. Note that all efflux pumps that survived the competition show good performance in the presence of α-pinene (FIG. 6). Measurements were taken in triplicate and averaged; error bars show standard deviation. All data are normalized to the final cell density of the negative control strain with 0% α-pinene.
Figure 3:
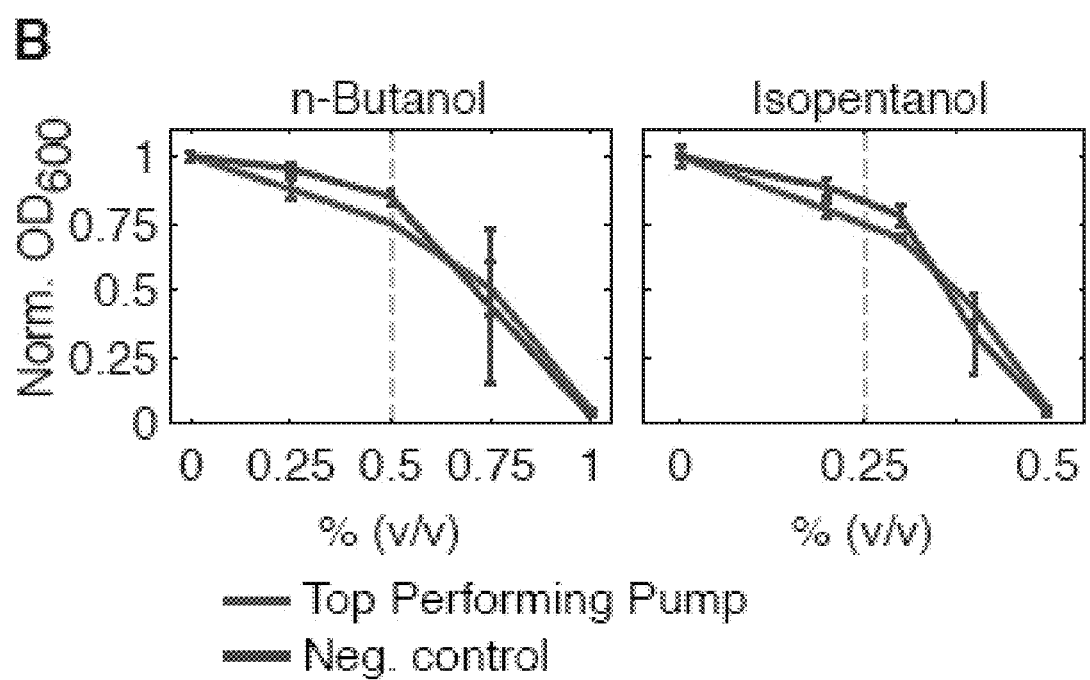
Figure 3:
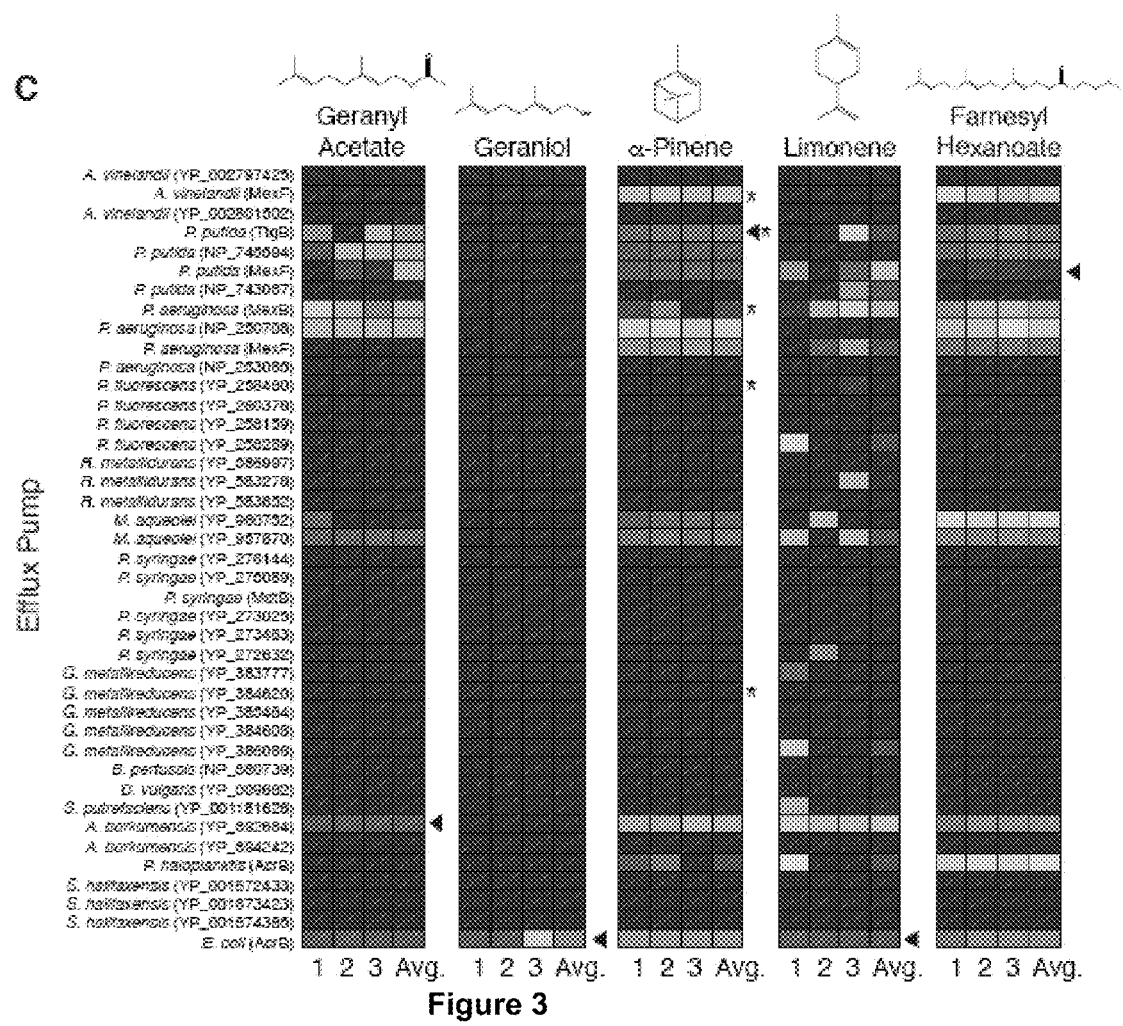
Figure 3:
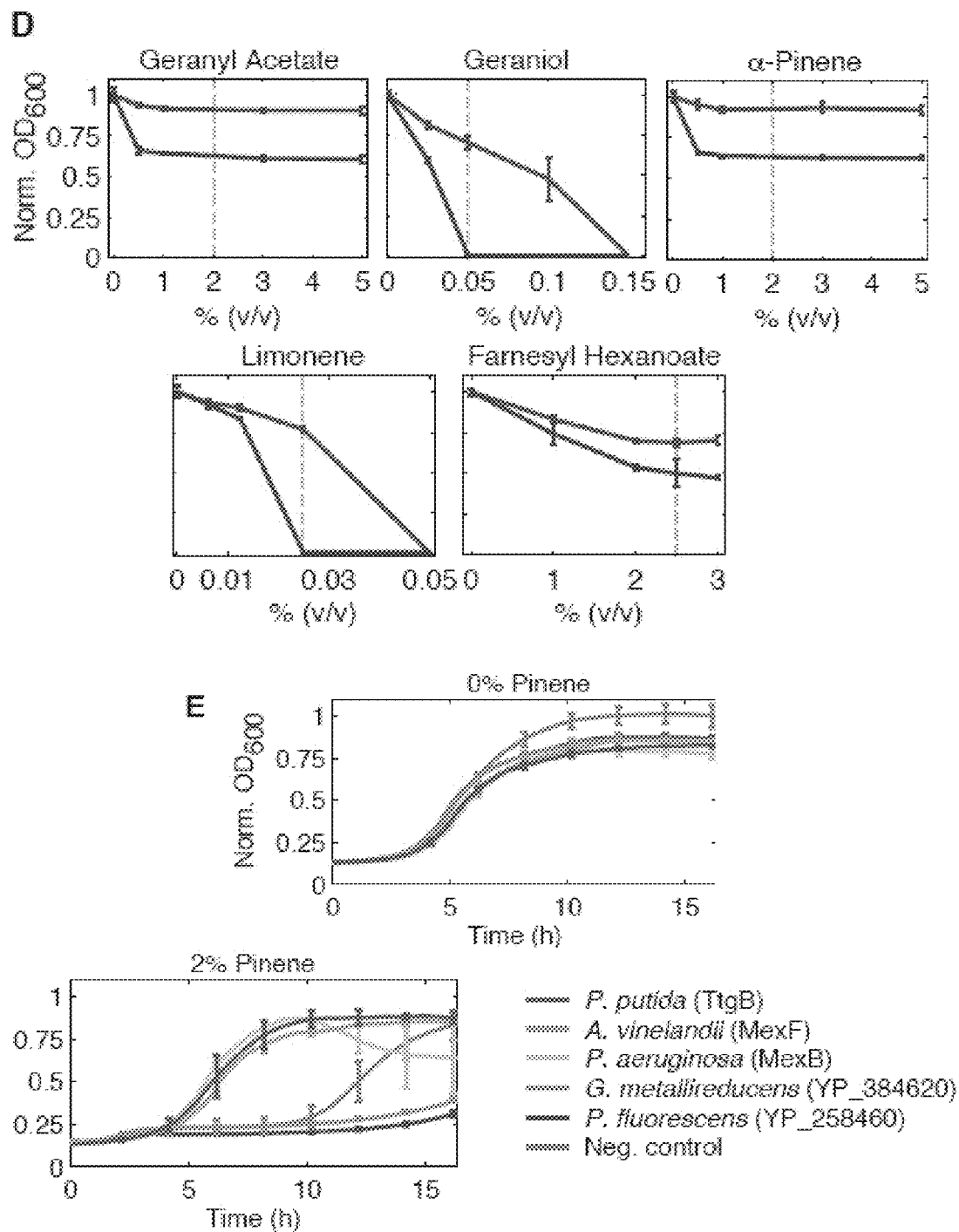

Next, we asked whether competing our cultures in the presence of different biofuels would identify unique sets of resistant efflux pumps for each biofuel. Our results fall broadly into two classes: (i) those where the biofuel is toxic, but pumps do not reduce toxicity and (ii) those where the pumps do reduce toxicity. Both n-butanol and isopentanol fall into the first class of fuels; they are toxic, but none of the pumps we tested confer an advantage (FIGS. 3A-B). This could be because none of the pumps in the library export these compounds or, alternatively, the rate of export may not be sufficient to counteract intracellular accumulation. Interestingly, n-butanol stress has been shown to upregulate efflux pump expression [14, 22], but our results clearly show that these pumps do not reduce stress. The second class of biofuels contains larger molecules that are toxic to cell growth, but where efflux pumps do improve tolerance. Here we see a distinct separation between the competition winners and those pumps that are not beneficial (FIG. 3C). We find that the competition survivors and their relative rankings are biofuel-specific.

We further characterized the competition winners by testing pump-expressing strains individually and comparing their survival relative to a pump-free negative control strain. For all biofuels, we chose the top performing pump and measured its survival relative to the control (FIG. 3D). All competition winners outperformed the control strain, and in some cases, such as with α-pinene and geranyl acetate, the pumps essentially confer immunity to the biofuel. Limonene and geraniol are both quite toxic, but these data show that pumps can still increase survival several-fold. In a production environment, pumps will export biofuel as it is produced, so even modest improvements in tolerance may be able to relieve the toxic burden of producing biofuel.

The competition winners for the range of biofuels illustrate how beneficial efflux pumps can come from a variety of host microbes. The best pump we found for geranyl acetate is YP_692684 from *Alcanivorax borkumensis* SK2, which is between 64-69% similar to AcrB, TtgB, and MexB (Table 2). Both geraniol and limonene are best exported by *E. coli* AcrB. Since we were testing the pumps in a ΔacrAB background the plasmid-based copy is providing the observed resistance, however in production strains AcrAB may be a good target for overexpression. The top performing α-pinene pump is TtgB and the best farnesyl hexanoate pump is MexF, both from *Pseudomonas putida* KT2440. Close behind these top-ranked pumps are several others that survived nearly as well, most of which have not been characterized for biofuel tolerance, or solvent tolerance in general.

For example, marine microbes like *M. aqueolei* and *A. borkumensis* appear to be valuable sources of biofuel-tolerant efflux pumps. Pumps from these organisms that export biofuel are similar (40-69%) to several known solvent-tolerant pumps, but it is not clear whether their substrate specificity is limited (like TtgB) or broad (like AcrB) (Table 2). Interestingly, several of the biofuel-tolerant pumps only have the inner membrane and periplasmic proteins on their plasmid, meaning that they must successfully recruit a native *E. coli* outer membrane protein for export [23].

TABLE 2

Percent homology of biofuel competition winners to efflux pumps with known solvent resistance properties. Homology results are calculated by comparing the entire amino acid sequences of the inner membrane proteins using BLAST.

| | E. coli AcrB | P. putida TtgB | P. aeruginosa MexB | P. aeruginosa MexD | P. aeruginosa MexF |
|---|---|---|---|---|---|
| A. vinelandii (MexF) | 42 | 41 | 40 | 41 | 85 |
| P. putida (TtgB) | 65 | 100 | 78 | 50 | 42 |
| P. putida (NP_745594) | 53 | 53 | 53 | 60 | 43 |
| P. putida (MexF) | 41 | 41 | 41 | 40 | 88 |
| P. aeruginosa (mexB) | 70 | 78 | 100 | 49 | 41 |
| P. aeruginosa (NP_250708) | 51 | 49 | 50 | 52 | 41 |
| P. aeruginosa (MexF) | 40 | 42 | 41 | 40 | 100 |
| P. fluorescens (YP_258460) | 66 | 87 | 79 | 79 | 40 |
| M. aqueolei (YP_960752) | 59 | 65 | 65 | 49 | 41 |

TABLE 2-continued

Percent homology of biofuel competition winners to efflux pumps with known solvent resistance properties. Homology results are calculated by comparing the entire amino acid sequences of the inner membrane proteins using BLAST.

|  | E. coli AcrB | P. putida TtgB | P. aeruginosa MexB | P. aeruginosa MexD | P. aeruginosa MexF |
|---|---|---|---|---|---|
| M. aqueolei (YP_957870) | 59 | 53 | 56 | 48 | 40 |
| A. borkumensis (YP_692684) | 69 | 64 | 66 | 50 | 41 |
| E. coli (AcrB) | 100 | 65 | 70 | 49 | 40 |

We selected the bio-jet fuel precursor α-pinene to assess the results of the competition assay more completely. A strong prediction of the mathematical model is that any performance disparities between competing strains will quickly be amplified so that under-performers are essentially eliminated from the population. Thus, strains that survive the competition will be both (i) the top performers and (ii) very similar in ability.

We tested these predictions experimentally by growing the α-pinene competition winners independently in the presence and absence of α-pinene. As predicted, all efflux pumps that remained at the end of the competition survive in the presence of α-pinene and have very similar growth profiles. Based on these data, we expect that all competition survivors shown in FIG. 3C will be good candidates for transporting their respective biofuels.

In order to verify that the competition sorted the efflux pumps correctly, we also tested representatives that did not survive the competition and one borderline case. In the absence of α-pinene, individual cultures with efflux pumps grow similarly, though not quite as well as the pump-free negative control (FIG. 3E). With α-pinene present, the top performer, P. putida TtgB, and a lower-ranked competition survivor, A. vinelandii MexF, both grow well. P. aeruginosa MexB is a borderline survivor that showed low, but detectable levels in two of the replicates (FIG. 3C). When grown independently the strain survives well in α-pinene for the first 10 hours, but after this point the cells begin to lyse and form aggregates (data not shown), causing the optical density of the culture to drop.

Two efflux pumps that did not survive the competition both grow poorly in the cultures with α-pinene. In fact, the negative control outperforms these two strains, likely due to the burden of pump expression acting in combination with α-pinene toxicity. Interestingly, the inner membrane protein one of the competition losers (P. fluorescens YP_258460) is highly similar (87%) to the top-ranked α-pinene pump (P. putida TtgB), but performs very poorly in cultures with α-pinene (Table 2). These data verify that the competitive growth assay provides an efficient method for screening efflux pumps for their ability to improve biofuel tolerance.

As metabolic engineering efforts continue to increase biofuel production titers it will be crucial to relieve the limitation presented by toxicity. Recent advances in genomic sequencing methods have led to dramatic increases in the number of sequenced organisms. We use this naturally occurring database of genes as a starting point to search for transporters that can increase biofuel tolerance. Our findings include several previously uncharacterized pumps from recently sequenced microbes. The competitive growth strategy allows us to efficiently separate out beneficial genes by relying on competitive exclusion of non-beneficial candidates. Additional methods for improvement, such as codon optimization or directed evolution can be used in the future to fine-tune these efflux pumps for a specific target. It should also be noted that the library generation and competition strategies are both generally applicable and not specific to efflux pumps or biofuel tolerance.

Efforts towards improving biofuel production to date have mainly focused on the metabolic pathways used to produce biofuel [24, 25]. However, when the production target is toxic, pathway optimization alone will eventually reach a point beyond which growth inhibition limits production titer. Even in the case of non-toxic target compounds, intracellular accumulation will ultimately limit production. Chassis engineering complements metabolic engineering efforts that focus on the fuel production pathway and will provide valuable strategies for improving biofuel yields.

The ability to engineer biofuel tolerance using efflux pumps may facilitate future improvements in microbial biofuel production. For several of the biofuels that we tested we have identified more than one efflux pump that increases tolerance. There is some evidence suggesting that pumps can work additively, and in some cases multiplicatively, to export substrates [26]; it would be interesting to test multi-pump constructs in the future.

Additionally, the library contains pumps with varying substrate specificities, which allows for investigation into the structural differences that contribute to substrate specificity. Efflux pumps show great promise as biofuel transporters and are a valuable tool for engineering biofuel-tolerant production strains.

Methods

Efflux Pump Selection.

Pumps were ranked based on their homology to the solvent resistance pump TtgB from *Pseudomonas putida* [12] (FIG. 4). The search space included all efflux pump genes annotated as members of the HAE1 family (TIGR00915) from all sequenced bacterial genomes, as listed in MicrobesOnline.org [27]. To avoid biases due to homology in the transmembrane regions, the homology search was limited to the amino acids in the two large periplasmic loops, which are the regions primarily responsible for substrate recognition [17]. Periplasmic loops were identified using the TMHMM software [28]; the homology searches were conducted using BLAST [29]. Custom scripts were written to automate the periplasmic loop identification and subsequent homology searches. From the ranked list of efflux pumps, representative pumps were selected that span the range of all efflux pumps in terms of both low and high homology to ttgB (FIG. 4). For each pump construct we included the proximal genes that contain the periplasmic linker and outer membrane protein, as long as they were on the same operon. In some cases only genes for the inner membrane and periplasmic linker proteins were present on the operon (e.g. NP_745594), and in a few cases there were additional copies of pump components, which were included in the constructs as long as they were on a contiguous operon (e.g. YP_274832). A complete list of the efflux pumps used in this experiment is provided in Table 1.

Strain and Plasmid Construction.

E. coli DH1 ΔacrAB was used as the base strain for all experiments. Efflux pump operons were cloned into a vector containing the medium copy p15A origin of replication, kanamycin resistance marker, lac/repressor, and IPTG-inducible lacUV5 promoter (FIG. 7, additional details in Supporting Methods).

Preparing Pooled Cultures.

Cells containing the efflux pump plasmids were individually adapted to M9 minimal medium (per liter: 200 ml 5×M9 salts, 2 ml 1M MgSO4, 50 ml 20% glucose, 20 ml 5% Casamino acids, 100 μl 0.5% Thiamine, 100 μl 1M CaCl2), as described in the Supporting Methods. At the conclusion of the adaptation period, the optical densities (absorbance at 600 nm) of the cultures were normalized and cultures were combined in equal proportion. This pooled culture was used to prepare single-use glycerol stocks.

Competitive Growth Assays.

Pooled culture glycerol stocks were used to inoculate M9 minimal medium with 30 μg/ml kanamycin and 10 μM IPTG. The culture was then divided into tubes to a final volume of 5 ml and biofuel was added directly to the tubes. All conditions were prepared in triplicate. Cultures were grown at 37° C. with orbital shaking at 200 rpm for all experiments.

In all cases, biofuel was added at a level that inhibited growth (v/v: 0.5% n-butanol; 0.25% isopentanol; 2% geranyl acetate; 0.05% geraniol; 2% α-pinene; 0.025% limonene; 2.5% farnesyl hexanoate), see also Supporting Methods. Because we were working with compounds with very different solubility and toxicity profiles there was no single criterion that applied to all, but in general we aimed to select an inhibitory concentration that reduced growth by 25% while maximizing the difference between the survival of the pool and negative control. FIGS. 3B and D show toxicity profiles for the best efflux pump and the negative control for each of the compounds tested.

Every 10-14 hours the cultures were diluted 1:100 into 5 ml of fresh M9 minimal medium with kanamycin, IPTG, and biofuel (where applicable). For the time-course assay, cultures were spun down at the completion of a growth cycle and plasmids were isolated. For end point competition assays, plasmid was isolated from the culture after 72 hours of serial dilution.

Microarray Design and Methods.

Custom microarrays (NimbleGen, Roche, USA) were used to measure the relative quantities of the efflux pumps present in the plasmid DNA isolated from the competition cultures. Arrays were designed so that they contained probes for all HAE1 annotated efflux pumps from all sequenced bacterial genomes. 12×135K arrays were used to allow for 12 experiments per slide.

Plasmid DNA was labeled and hybridized following the protocol for NimbleGen Comparative Genomic Hybridization Microarrays with minor modifications (Supporting Methods). Data were normalized using the standard settings for RMA analysis in the NimbleScan software. Probe values were averaged using a custom Matlab script (Mathworks, Inc.). Data for all efflux pumps are presented with the exception of two that we were unable to measure conclusively (Supporting Methods). For the positive hybridization control, all library plasmids were prepared individually and combined in vitro in equal proportions. For the negative hybridization control, a plasmid with the same vector backbone as those in the library, but no efflux pump, was isolated from DH1 ΔacrAB. Both hybridization controls were labeled and hybridized to the array using the methods described above.

Single-Strain Biofuel Toxicity Assays.

Individual strains were adapted to M9 minimal medium as described in the Supporting Methods. Adapted glycerol stocks were used to inoculate M9 minimal medium with 30 μg/ml kanamycin and 10 μM IPTG. The biofuel being tested was added directly to the cultures and they were grown overnight at 37° C. with orbital shaking. For end point measurements, the optical density was measured after 14 hours of growth in triplicate 5 ml cultures. For growth curve measurements, cultures were grown in triplicate in 24-well plates with 800 μl per well and optical density was measured every 10 minutes with a plate reader (BioTek Synergy 4, USA).

Mathematical Modeling.

The competitive Lotka-Volterra equation [19] was used to model growth of the pooled culture:

$$\frac{dN_i}{dt} = d_i N_i \left(1 - \sum_{j=1}^{c} \frac{A_{ij} N_j}{K}\right)$$

where Ni is the cell density of strain i, di is the growth rate of strain i, and K is the carrying capacity of the entire culture. A is the interaction matrix, where we assume $$A_{ij} = \frac{d_j}{d_i}.$$

Parameters are given in the figure legends. Individual (non-competitive) simulations set the initial conditions to zero for all but one strain; competitive growth simulations set the initial conditions to be equal, for all strains. All simulations were done in Matlab (Math Works, Inc., Natick, Mass.).

TABLE 1

| EPL # | Organism | Source | NCBI Accession* | Synonynms* | VIMSS ID* | Operon length |
|---|---|---|---|---|---|---|
| 2 | Azotobacter vinelandii AvOP | ATCC BAA-1303 | YP_002797425 | Avin_01890 | 2257055, 6916632 | 4318 |
| 3 | Azotobacter vinelandii AvOP | ATCC BAA-1303 | YP_002800512 | mexF, Avin_33870 | 2257195, 6919831 | 4409 |
| 4 | Azotobacter vinelandii AvOP | ATCC BAA-1303 | YP_002801502 | Avin_44060 | 2259215, 6920854 | 4490 |
| 11 | Pseudomonas putida KT2440 | From lab stock | NP_743544 | ttgB, PP_1385 | 217080 | 5762 |
| 12 | Pseudomonas putida KT2440 | From lab stock | NP_745594 | PP_3456 | 219130 | 4316 |
| 14 | Pseudomonas putida KT2440 | From lab stock | NP_745564 | mexF, PP_3426 | 219100 | 5846 |

TABLE 1-continued

| EPL # | Organism | Source | NCBI Accession* | Synonynms* | VIMSS ID* | Operon length |
|---|---|---|---|---|---|---|
| 15 | *Pseudomonas putida* KT2440 | From lab stock | NP_743067 | PP_0906 | 216603 | 4267 |
| 32 | *Pseudomonas aeruginosa* PAO1 | ATCC 47085D-5 | NP_249117 | mexB, PA_0426 | 56877 | 5767 |
| 33 | *Pseudomonas aeruginosa* PAO1 | ATCC 47085D-5 | NP_250708 | PA_2018 | 58468 | 4344 |
| 36 | *Pseudomonas aeruginosa* PAO1 | ATCC 47085D-5 | NP_251184 | mexF, PA2494 | 58944 | 5870 |
| 37 | *Pseudomonas aeruginosa* PAO1 | ATCC 47085D-5 | NP_253065 | PA_4375 | 60825 | 4238 |
| 42 | *Pseudomonas fluorescens* Pf-5 | ATCC BAA-477D | YP_258460 | PFL_1331 | 871967 | 5801 |
| 43 | *Pseudomonas fluorescens* Pf-5 | ATCC BAA-477D | YP_260376 | PFL_3271 | 873906 | 4263 |
| 45 | *Pseudomonas fluorescens* Pf-5 | ATCC BAA-477D | YP_258159 | PFL_1028 | 871664 | 4211 |
| 48 | *Pseudomonas fluorescens* Pf-5 | ATCC BAA-477D | YP_258289 | PFL_1158 | 871794 | 4152 |
| 52 | *Ralstonia metallidurans* CH34 | ATCC 43123D-5 | YP_586997 | Rmet_4866 | 1777246 | 6025 |
| 53 | *Ralstonia metallidurans* CH34 | ATCC 43123D-5 | YP_583276 | Rmet_1121 | 1773525 | 3135 |
| 54 | *Ralstonia metallidurans* CH34 | ATCC 43123D-5 | YP_583852 | Rmet_1702 | 1774101 | 5884 |
| 55 | *Marinobacter aqueolei* | ATCC 700491D-5 | YP_960752 | Maqu_3494 | 3525043 | 4269 |
| 56 | *Marinobacter aqueolei* | ATCC 700491D-5 | YP_957870 | Maqu_0582 | 3522072 | 5841 |
| 59 | *Pseudomonas syringae phaseolicola* | ATCC BAA-978D | YP_276144 | PSPPH_4014 | 880881 | 5789 |
| 61 | *Pseudomonas syringae phaseolicola* | ATCC BAA-978D | YP_275089 | PSPPH_2907 | 879774 | 4338 |
| 63 | *Pseudomonas syringae phaseolicola* | ATCC BAA-978D | YP_274832 | mdtB, PSPPH_2641 | 879508 | 9036 |
| 64 | *Pseudomonas syringae phaseolicola* | ATCC BAA-978D | YP_273025 | PSPPH_0733 | 877600 | 4175 |
| 65 | *Pseudomonas syringae phaseolicola* | ATCC BAA-978D | YP_273463 | PSPPH_1196 | 878063 | 4268 |
| 66 | *Pseudomonas syringae phaseolicola* | ATCC BAA-978D | YP_272632 | PSPPH_0329 | 877196 | 5302 |
| 67 | *Geobacter metallireducens* GS-15 | ATCC 53774D-5 | YP_383777 | Gmet_0810 | 1089291 | 6036 |
| 68 | *Geobacter metallireducens* GS-15 | ATCC 53774D-5 | YP_384620 | Gmet_1664 | 1090164 | 6053 |
| 69 | *Geobacter metallireducens* GS-15 | ATCC 53774D-5 | YP_385464 | Gmet_2518 | 1091030 | 5642 |
| 70 | *Geobacter metallireducens* GS-15 | ATCC 53774D-5 | YP_384608 | Gmet_1652 | 1090152 | 5874 |
| 71 | *Geobacter metallireducens* GS-15 | ATCC 53774D-5 | YP_386066 | Gmet_3127 | 1091646 | 5848 |
| 84 | *Bordetella pertussis* Tohama 1 | ATCC BAA-589D-5 | NP_880739 | BP_2076 | 513353 | 6138 |
| 90 | *Desulfovibrio vulgaris* Hildenborough | From lab stock | YP_009662 | DVU_0438 | 209374 | 4583 |
| 92 | *Shewanella putrefaciens* CN-32 | ATCC BAA-1097 | YP_001181626 | Sputcn32_0091 | 3436721 | 4290 |
| 95 | *Alcanivorax borkumensis* SK2 | ATCC 700651 | YP_692684 | AcrB/AcrD/AcrFa, ABO_0964 | 2080634 | 5927 |
| 96 | *Alcanivorax borkumensis* SK2 | ATCC 700651 | YP_694242 | ABO_2522 | 2082192 | 4297 |
| 100 | *Shewanella halifaxensis* HAW-EB4 | DSM 17350 | YP_001672433 | Shal_0198 | 3784053 | 4320 |
| 101 | *Shewanella halifaxensis* HAW-EB4 | DSM 17350 | YP_001673423 | Shal_1195 | 3785066 | 4487 |
| 102 | *Shewanella halifaxensis* HAW-EB4 | DSM 17350 | YP_001674385 | Shal_2167 | 3786103 | 5892 |
| 122 | *Escherichia coli* K12 MG1655 | From lab stock | NP_417732 | acrF | 17336 | 4274 |
| 123 | *Escherichia coli* K12 MG1655 | From lab stock | NP_414995 | acrB | 14599 | 4366 |
| 124 | *Escherichia coli* K12 MG1655 | From lab stock | NP_416965 | acrD | 16569 | 3114 |

*The NCBI/GenBank Accession No. provided herein refers to only the inner membrane protein of the operon encoding all of the proteins of the corresponding efflux pump. The entire nucleotide sequence of the operon is used in the construct in order to express all of the proteins of each efflux pump.

Supporting Methods

Strain and Plasmid Construction.

The acrAB operon was knocked out of the chromosome of *E. coli* DH1 using recombineering methods from (Datsenko, K. A. and B. L. Wanner, *One-step inactivation of chromosomal genes in Escherichia coli K-12 using PCR products*. Proceedings Of The National Academy Of Sciences Of The United States Of America, 2000. 97(12): p. 6640-6645) with the homology primers for acrA and acrB from Baba, T., et al. (*Construction of Escherichia coli K-12 in-frame, single-gene knockout mutants: the Keio collection*. Molecular Systems Biology, 2006). To prepare the inserts containing the efflux pump operons genomic DNA or the microbe of interest was obtained from ATCC, DSMZ, or individual researchers (Table 1). Where necessary genomic DNA was isolated using the DNA Blood and Tissue Kit (Qiagen Inc., Valencia, Calif.).

The overall cloning strategy is summarized in FIG. 7. Efflux pump operons were amplified from genomic DNA using primers with short linker sequences (Table 1). PCR products were then gel extracted and used as the template for a second PCR reaction to attach homology arms for the vector backbone. For all, the second PCR reaction used the forward primer 5'-caaaagatcttttaagaaggagatatacat-3' (SEQ ID NO:7) and reverse primer 5'-gcctggagatccttactcgagtttg-gatcctcagtggtgatggtgatgatg-3' (SEQ ID NO:6). The PCR products were gel extracted, treated with T4, and annealed following the protocol in Li, M. Z., et al. (*Harnessing homologous recombination in vitro to generate recombinant DNA via SLIC*. Nature Methods, 2007. 4(3): p. 251-256). A vector backbone with p15A medium copy origin, kan$^R$, lacI, and lacUV5 promoter was used for all plasmid constructs (see FIG. 7). The vector was treated with T4 and annealed to the insert following Li, M. Z., et al. Ligated products were transformed into Top10 cells (Invitrogen) and plated on 50 μg/ml kanamycin plates. Colonies were screened by preparing plasmids and conducting end-read sequencing to check the integrity of the two ligation points. Successful clones were subsequently sequenced in entirety. Of these, several had point mutations (listed in Table 1), though most (35 out of 43) were not in conserved regions. Although high fidelity polymerases (Phusion, Finnzymes; PfuUltra II Fusion, Stratagene) were used for the amplification, mutations could be the result of the large amplicon size, high GC content, or incorrect genomic reference sequence. Plasmids were transformed into DH1 ΔacrAB cells for use in all future experiments.

Adaptation to M9 Minimal Medium.

Prior to adaptation, cells grown on M9 minimal medium experience an extended lag phase relative to growth in LB medium. This lag can be eliminated by adapting cells to the minimal medium. *E. coli* DH1 ΔacrAB cells containing the efflux pump plasmids were inoculated from single colonies into selective LB medium and grown overnight at 37° C. with orbital shaking at 200 rpm. Each of these 43 cultures was then diluted 1:100 into 5 ml of fresh M9 minimal medium and 30 μg/ml kanamycin and incubated at 37° C. with shaking. The dilution step was repeated every 24 hours for a total of 72 hours. Upon completion of the adaptation, cultures grown on M9 minimal medium showed similar growth profiles to those grown on LB medium.

Competitive Growth Assays.

The toxicity of limonene and geraniol were high and very small quantities were needed for the assay. This required the use of a co-solvent in order to accurately pipette small volumes. In both cases dimethylformamide (DMF) was used as the co-solvent. The amount of DMF present in the culture was always less than 0.2%, which is significantly under the toxicity limit to E. coli. Other biofuels were added directly without the use of a co-solvent.

Microarray Design and Methods.

Plasmid DNA was labeled following the protocol for NimbleGen Comparative Genomic Hybridization Microarrays with the following modifications: ¼-size reactions were found to be sufficient to yield enough labeled DNA. After addition of stop solution, samples were purified using a PCR purification column (Qiagen). 2 µg of Cy3-labeled DNA was hybridized to the array following the NimbleGen protocol. Although the library contains plasmids for the native E. coli efflux pumps AcrEF and AcrD we were not able to measure their quantities conclusively. We found that chromosomal copies of these two operons carried through into the plasmid preparation and were labeled and hybridized to the array, causing positive hits on the negative hybridization control. Because the amount of genomic DNA present differed with each plasmid preparation the results for these two pumps are not accurate representations of the plasmid-based quantities and have been omitted from the figures. Because we were working in a ΔacrAB background this same problem did not apply to E. coli AcrAB.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A modified host cell comprising: (a) an efflux pump comprising an amino sequence having at least 95% identity as compared to the amino acid sequence of *Azotobacter vinelandii* AvOP MexEF, *Pseudomonas putida* KT2440 TtgABC, *Pseudomonas putida* KT2440 MexEF-OprN, *Pseudomonas aeruginosa* PA01 MexAB-OprM, *Pseudomonas aeruginosa* PA01 MexEF-OprN, *Escherichia coli* K12 AcrAB, *Pseudomonas putida* KT2440 NP_745594, *Pseudomonas aeruginosa* PA01 NP_250708, *Marinobacter aqueolei* YP_960752, *Marinobacter aqueolei* YP_957870, or *Alcanivorax borkumensis* SK2 YP_692684, wherein said efflux pump is heterologous to the modified host cell, and capable of transportation of an organic molecule out of the modified host cell, and (b) a recombinant nucleic acid encoding one or more enzymes for producing the organic molecule; wherein the organic molecule at a sufficiently high concentration inhibits or reduces the growth rate of or is lethal to the modified host cell, the modified host cell is a bacterium and the organic molecule is a C4-C12 alcohol, pinene, geranyl acetate, geraniol, limoene, or faresyl hexanoate.

2. The modified host cell of claim 1, wherein the efflux pump comprises an amino acid sequence having at least 99% identity as compared to the amino acid sequence of *Azotobacter vinelandii* AvOP MexEF, *Pseudomonas putida* KT2440 TtgABC, *Pseudomonas putida* KT2440 MexEF-OprN, *Pseudomonas aeruginosa* PA01 MexAB-OprM, *Pseudomonas aeruginosa* PA01 MexEF-OprN, *Escherichia coli* K12 AcrAB, *Pseudomonas putida* KT2440 NP_745594, *Pseudomonas aeruginosa* PA01 NP_250708, *Marinobacter aqueolei* YP_960752, *Marinobacter aqueolei* YP_957870, or *Alcanivorax borkumensis* SK2 YP_692684.

3. The modified host cell of claim 2, wherein the efflux pump comprises an amino acid sequence identical to the amino acid sequence of *Azotobacter vinelandii* AvOP MexEF, *Pseudomonas putida* KT2440 TtgABC, *Pseudomonas putida* KT2440 MexEF-OprN, *Pseudomonas aeruginosa* PA01 MexAB-OprM, *Pseudomonas aeruginosa* PA01 MexEF-OprN, *Escherichia coli* K12 AcrAB, *Pseudomonas putida* KT2440 NP_745594, *Pseudomonas aeruginosa* PA01 NP_250708, *Marinobacter aqueolei* YP_960752, *Marinobacter aqueolei* YP_957870, or *Alcanivorax borkumensis* SK2 YP_692684.

4. The modified host cell of claim 1, wherein the efflux pump is able to export the organic molecule from the modified host cell using the proton motive force.

5. The modified host cell of claim 4, wherein the efflux pump has the amino acid sequence of SEQ ID NO:1, 2, 3, or 4.

6. The modified host cell of claim 4, wherein the organic molecule is geraniol, and the efflux pump is encoded by *Escherichia coli* K12 operon encoding AcrAB.

7. The modified host cell of claim 4, wherein the organic molecule is limonene, and the efflux pump is encoded by *Pseudomonas putida* KT2440 MexEF-OprN, *Pseudomonas aeruginosa* PA01 MexAB-OprM, *Marinobacter aqueolei* operon encoding YP_957870, *Alcanivorax borkumensis* SK2 operon encoding YP_692684, or *Escherichia coli* K12 operon encoding AcrAB.

8. The modified host cell of claim 1, wherein the efflux pump is comprises an amino sequence identical to the amino acid sequence of *Pseudomonas aeruginosa* PA01 MexAB-OprM, *Pseudomonas putida* KT2440 MexEF-OprN, *Pseudomonas putida* KT2440 TtgABC, or *Escherichia coli* K12 AcrAB.

9. The modified host cell of claim 1, wherein the organic molecule is α-pinene or farnesyl hexanoate, and the efflux pump comprises an amino sequence identical to the amino acid sequence of is *Azotobacter vinelandii* AvOP MexEF, *Pseudomonas putida* KT2440 TtgABC, *Pseudomonas putida* KT2440 MexEF-OprN, *Pseudomonas aeruginosa* PA01 MexAB-OprM, *Pseudomonas aeruginosa* PA01 MexEF-OprN, *Escherichia coli* K12 AcrAB, *Pseudomonas putida* KT2440 NP_745594, *Pseudomonas aeruginosa* PA01 NP_250708, *Marinobacter aqueolei* YP_960752, *Marinobacter aqueolei* YP_957870, or *Alcanivorax borkumensis* SK2 YP_692684.

10. The modified host cell of claim 1, wherein the organic molecule is geranyl acetate, geraniol, α-pinene, limoene, or faresyl hexanoate.

11. The modified host cell of claim 1, wherein the bacterium is a Gram-negative bacterium.

12. The modified host cell of claim 1, wherein the bacterium is of the genus *Planctomyces, Bradyrhizobium, Rhodobacter, Rhizobium, Myxococcus, Klebsiella, Azotobacter, Escherichia, Salmonella, Pseudomonas, Caulobacter, Chlamydia, Acinetobacter, Sinorhizobium, Vibrio*, or *Zymomonas*.

13. The modified host cell claim 1, wherein the efflux pump comprises an amino acid sequence having at least 95% identity as compared to the amino acid sequence of *Escherichia coli* K12 AcrAB.

14. The modified host cell claim 1, wherein the efflux pump comprises an amino acid sequence having at least 95% identity as compared to the amino acid sequence of *Pseudomonas putida* KT2440 TtgABC.

15. A method for culturing or growing the modified host cell of a present invention, comprising: (a) providing the modified host cell of claim 1, and (b) culturing or growing the modified host cell such that the efflux pump is expressed, such that the modified host cell has a growth rate or doubling time that is faster compared to the growth rate or doubling time of a cell identical to the modified host cell except that the cell does not express the efflux pump.

16. The method of claim 15, wherein the culturing or growing step (b) comprises culturing or growing the modified host cell in an environment comprising a sufficiently high concentration of the organic molecule such that the organic molecule inhibits or reduces the growth rate of or is lethal to the host cell.

17. The method of claim 16, wherein the separating step (c) comprises separating the liquid portion of the solution from the modified host cell in the solution.

18. The method of claim 15, wherein the method further comprises: (c) separating the organic molecule produced by the modified host cell, and pumped out of the host cell, from the host cell.

* * * * *